(12) United States Patent
Byrd et al.

(10) Patent No.: US 10,506,946 B2
(45) Date of Patent: Dec. 17, 2019

(54) MOTION BOX VISUALIZATION FOR ELECTROMAGNETIC SENSOR TRACKING SYSTEM

(71) Applicant: St. Jude Medical International Holding S.á r.l., Luxembourg (LU)

(72) Inventors: Charles B. Byrd, Oakdale, MN (US); Stavit Cohen, Haifa (IL); Alexander Gorovoy, Kiryat Motzkin (IL); Avinoam Romano, Ein Dor (IL)

(73) Assignee: St. Jude Medical International Holding S.ár.l., Luxembourg (LU)

( * ) Notice: Subject to any disclaimer, the term of this patent is extended or adjusted under 35 U.S.C. 154(b) by 302 days.

(21) Appl. No.: 15/380,786

(22) Filed: Dec. 15, 2016

(65) Prior Publication Data

US 2017/0164870 A1    Jun. 15, 2017

Related U.S. Application Data

(60) Provisional application No. 62/418,231, filed on Nov. 6, 2016, provisional application No. 62/267,772, filed on Dec. 15, 2015.

(51) Int. Cl.
*A61B 5/06* (2006.01)
*A61B 5/00* (2006.01)
(Continued)

(52) U.S. Cl.
CPC .............. *A61B 5/062* (2013.01); *A61B 5/746* (2013.01); *A61B 34/20* (2016.02); *A61B 34/25* (2016.02);
(Continued)

(58) Field of Classification Search
USPC .................................................. 600/424, 447
See application file for complete search history.

(56) References Cited

U.S. PATENT DOCUMENTS 6,233,476 B1    5/2001 Strommer et al.
6,498,944 B1    12/2002 Ben-Haim et al.
(Continued)

FOREIGN PATENT DOCUMENTS

| EP | 1944733 A2 | 7/2008 |
| JP | 2008-178686 A | 8/2008 |
| WO | 98/35720 A2 | 8/1998 |

OTHER PUBLICATIONS

European Patent Office; International Search Report and Written Opinion issued in counterpart International Application No. PCT/IB2016/057693. dated Mar. 20, 2017.

*Primary Examiner* — Nicole F Lavert
(74) *Attorney, Agent, or Firm* — Dykema Gossett PLLC

(57) ABSTRACT

Methods, systems, and apparatuses for visualizing the motion box of an electromagnetic sensor tracking system on a display that can be viewed by the physician are disclosed. Electromagnetic sensor tracking systems are able to determine the position and orientation (P&O) of the sensors being tracked only when the sensors are within the motion box, or the spatial region located in proximity to the electromagnetic field generators of the system. During usage of the electromagnetic sensor tracking system, the sensor can go out of this spatial region and, when this occurs, navigating it back into the motion box can be difficult. The methods, systems, and apparatuses described herein provide for the representation of sensors, the motion box, and a representation of a thorax on a display so that the clinician can view the position and orientation of the sensors with respect to the motion box.

20 Claims, 16 Drawing Sheets

(51) Int. Cl.
*A61B 34/20* (2016.01)
*A61B 34/00* (2016.01)
*A61B 90/00* (2016.01)
*A61B 34/10* (2016.01)

(52) U.S. Cl.
CPC . *A61B 2034/107* (2016.02); *A61B 2034/2051* (2016.02); *A61B 2090/376* (2016.02); *A61B 2576/00* (2013.01)

(56) References Cited

U.S. PATENT DOCUMENTS

| | | |
|---|---|---|
| 6,788,967 B2 | 9/2004 | Ben-Haim et al. |
| 7,197,354 B2 | 3/2007 | Sobe |
| 7,386,339 B2 | 6/2008 | Strommer et al. |
| 8,636,718 B2 | 1/2014 | Sela et al. |
| 2007/0299352 A1* | 12/2007 | Harlev ................. A61B 5/0422 600/509 |
| 2008/0183071 A1 | 7/2008 | Strommer et al. |
| 2014/0222409 A1 | 8/2014 | Efrat et al. |
| 2014/0275985 A1* | 9/2014 | Walker ................... A61B 5/062 600/424 |
| 2014/0275988 A1* | 9/2014 | Walker ................... A61B 5/061 600/424 |

\* cited by examiner

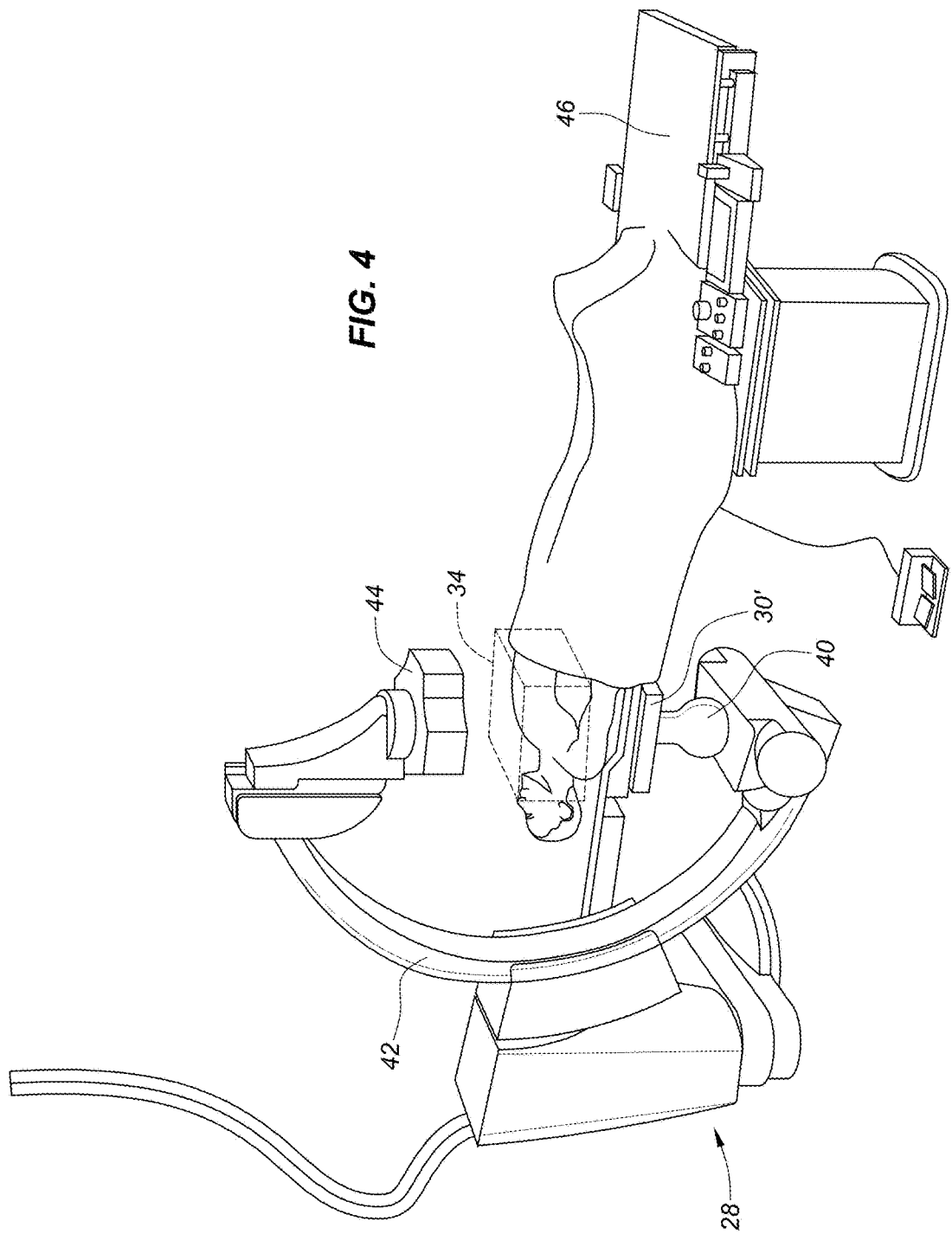

MOTION BOX VISUALIZATION FOR ELECTROMAGNETIC SENSOR TRACKING SYSTEM

CROSS-REFERENCE TO RELATED APPLICATIONS

This application claims the benefit of U.S. provisional application Nos. 62/267,772, filed on Dec. 15, 2015, and 62/418,231, filed on Nov. 6, 2016, which are hereby incorporated by reference as though fully set forth herein.

BACKGROUND a. Field

The present disclosure relates to a method and system for visualizing a motion box of an electromagnetic sensor tracking system.

b. Background Art

Many medical procedures require the introduction of specialized medical devices into and/or around the human heart. In particular, there are a number of medical procedures that require the introduction of specialized devices including, but not limited to, catheters, dilators, and needles to areas, such as into the atria or ventricles, to access the inner surface of the heart, or into the pericardial sac surrounding the heart to access the epicardium or outer surface of the heart. Catheters, guidewires, and access sheaths or introducers have been used for medical procedures for a number of years.

Interventional cardiologists or clinicians use electromagnetic sensor tracking systems during many medical procedures. During the usage of the electromagnetic sensor tracking system, the sensor can go out of the spatial region where the system is able to track the sensor (the "motion box"), and bringing it back to the region can be difficult. Accordingly, in existing systems, the clinician may lose the sensor, and it may be time consuming and/or difficult for the clinician to bring the sensor back into the motion box. This may result in the addition of unnecessary, and potentially harmful, time to the medical procedure. Furthermore, the loss of the sensor may force the clinician to take additional fluoroscopic images to find the sensor. This subjects the patient, as well as the clinician, to additional radiation.

There is, therefore, a need for MPS-enabled (or medical-positioning-system enabled) medical devices and methods of manufacture thereof that minimize or eliminate, for example, one or more of the problems set forth above.

BRIEF SUMMARY

One advantage of the methods, systems, and apparatuses described, depicted, and claimed herein relates to a visualization of the motion box on a display that can be viewed by the physician. Electromagnetic sensor tracking systems are able to determine the position and orientation (P&O) of the sensors being tracked only when the sensors are put within the motion box, or the spatial region located in proximity to the electromagnetic field generators of the system. During usage of the electromagnetic sensor tracking system, the sensor can go out of this spatial region (for example, when a physician navigates a tool to a location in a patient that is not within the portion of the magnetic field where accurately tracking is possible) and bringing it back can be difficult. Therefore, the disclosure is directed to a visualization of the motion box. The methods, systems, and apparatuses described herein provide for the representation of sensors, the motion box, and a representative thorax (used to, for example, 'visually orient' a system user) on a display so that the clinician can view the position and orientation of the sensors with respect to the motion box. This aids a clinician in maintaining a sensor within the motion box, and may reduce the time and/or number of additional fluoroscopic images it takes to return the sensor to the motion box, in the event the sensor exits the motion box.

These and other benefits, features, and capabilities are provided according to the structures, systems, and methods depicted, described, and claimed herein.

BRIEF DESCRIPTION OF EMBODIMENTS

FIG. 4 is a diagrammatic view of the system of FIG. 1 in an alternative embodiment of a catheter-lab environment.

FIG. 9B is diagrammatic view of the image panning and zooming shown in

FIG. 9A.

Figure 10:
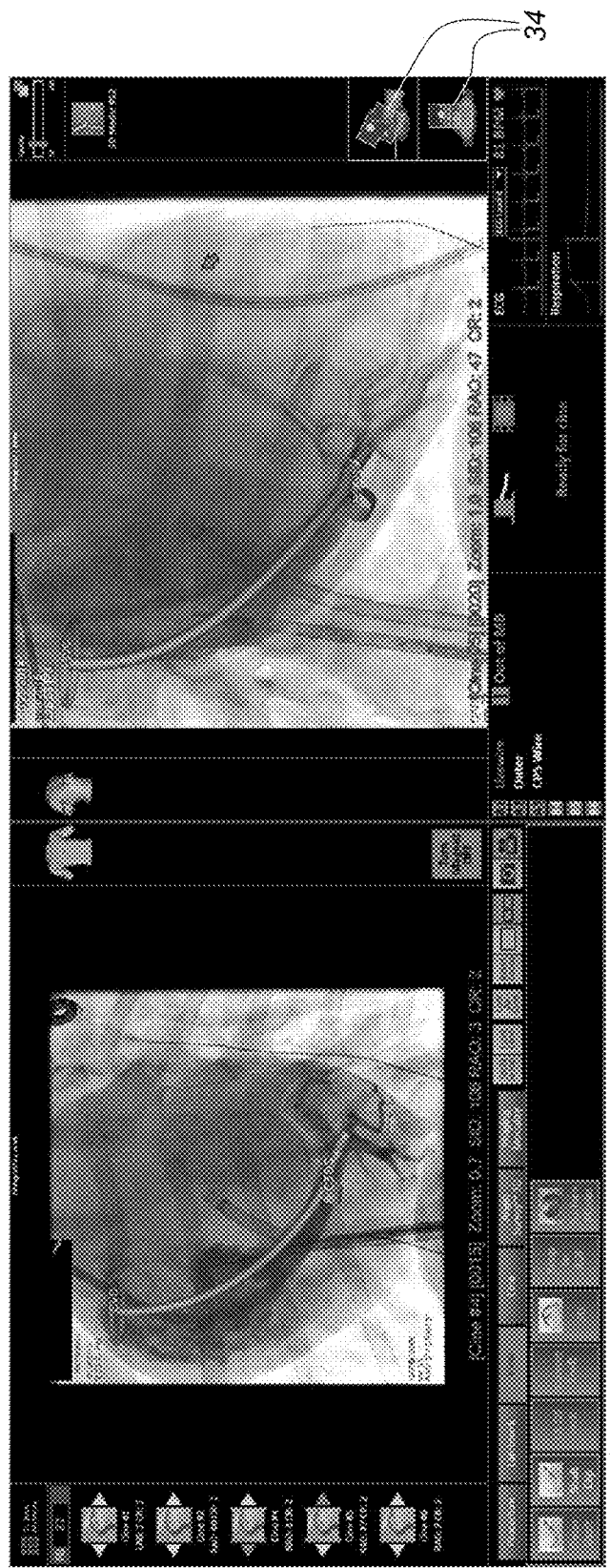

FIG. 10 is an image depicting the visualization of a motion box, a patient reference sensor, medical device sensor(s), and a thorax in reference to a table coordinate system alongside additional information relevant to a medical procedure.

Figure 11:
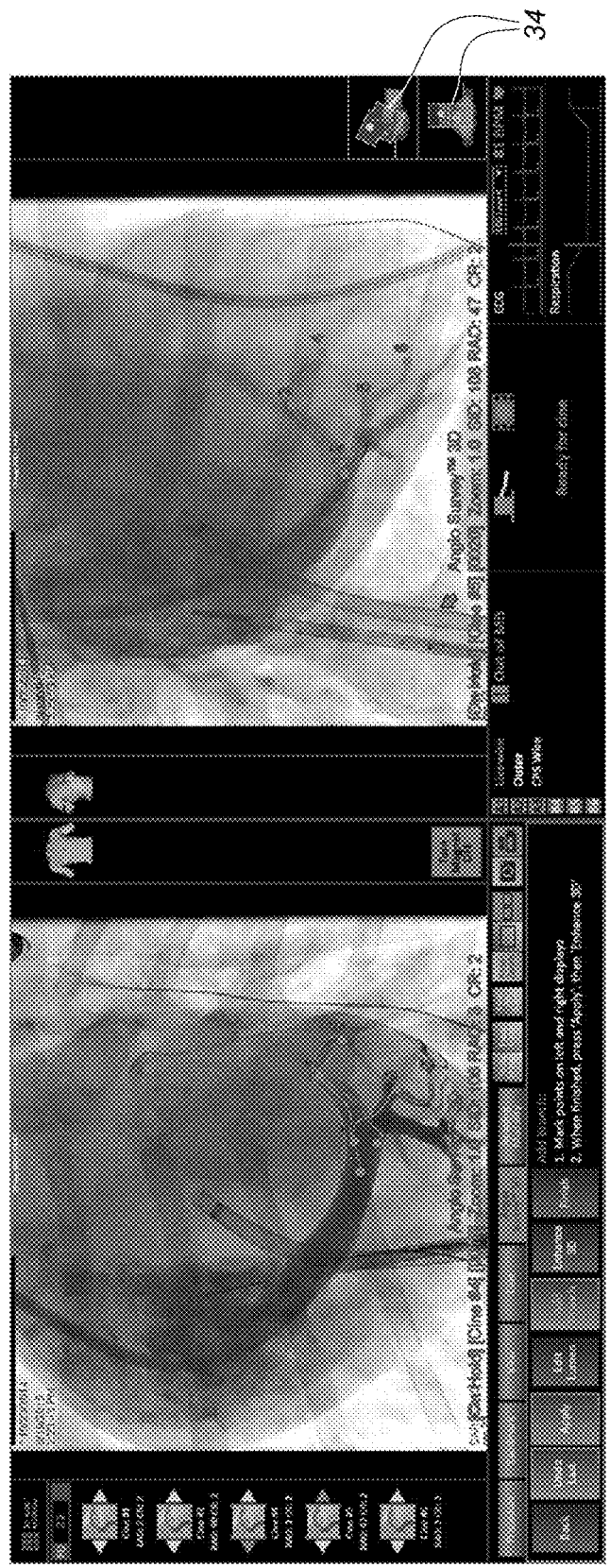

FIG. 11 is an image depicting the visualization of a motion box, a patient reference sensor, medical device sensor(s), and a thorax in reference to a table coordinate system alongside additional information relevant to a medical procedure.

Figure 12:
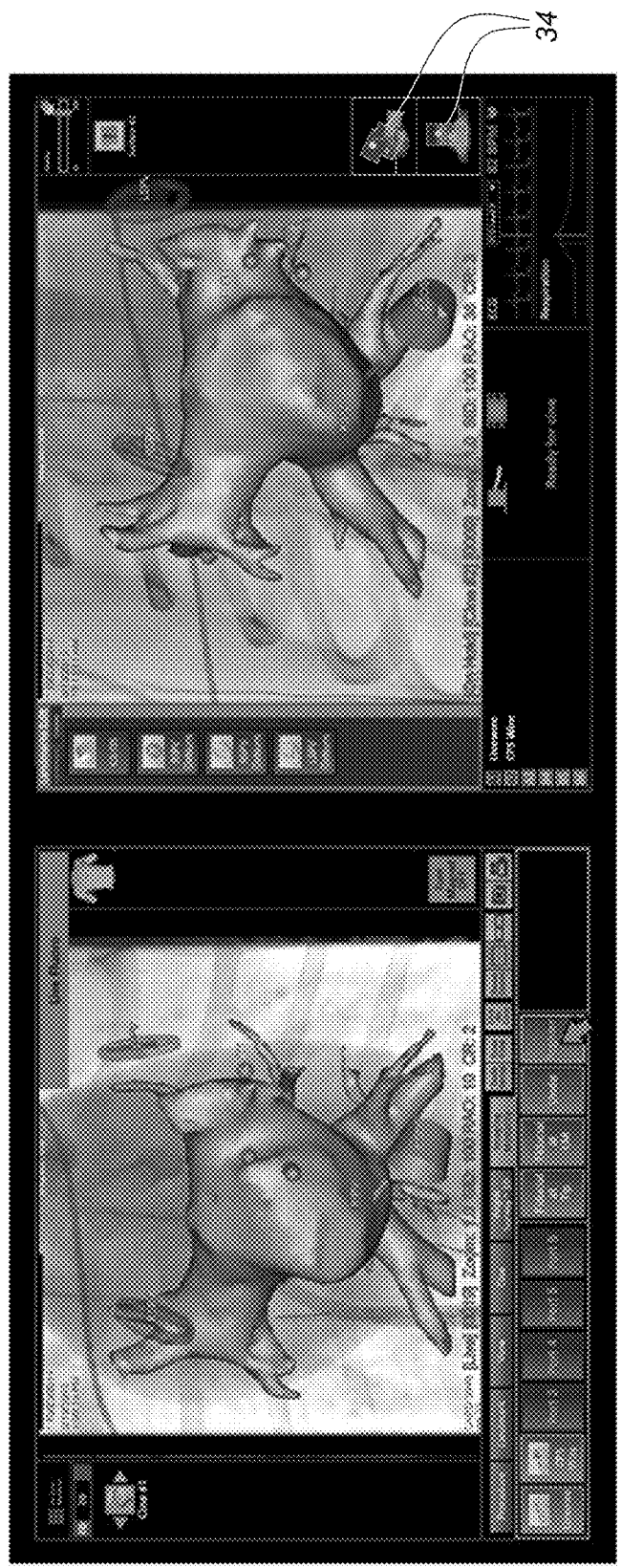

FIG. 12 is an image depicting the visualization of a motion box, a patient reference sensor, medical device sensor(s), and a thorax in reference to a table coordinate system alongside additional information relevant to a medical procedure.

Figure 13:
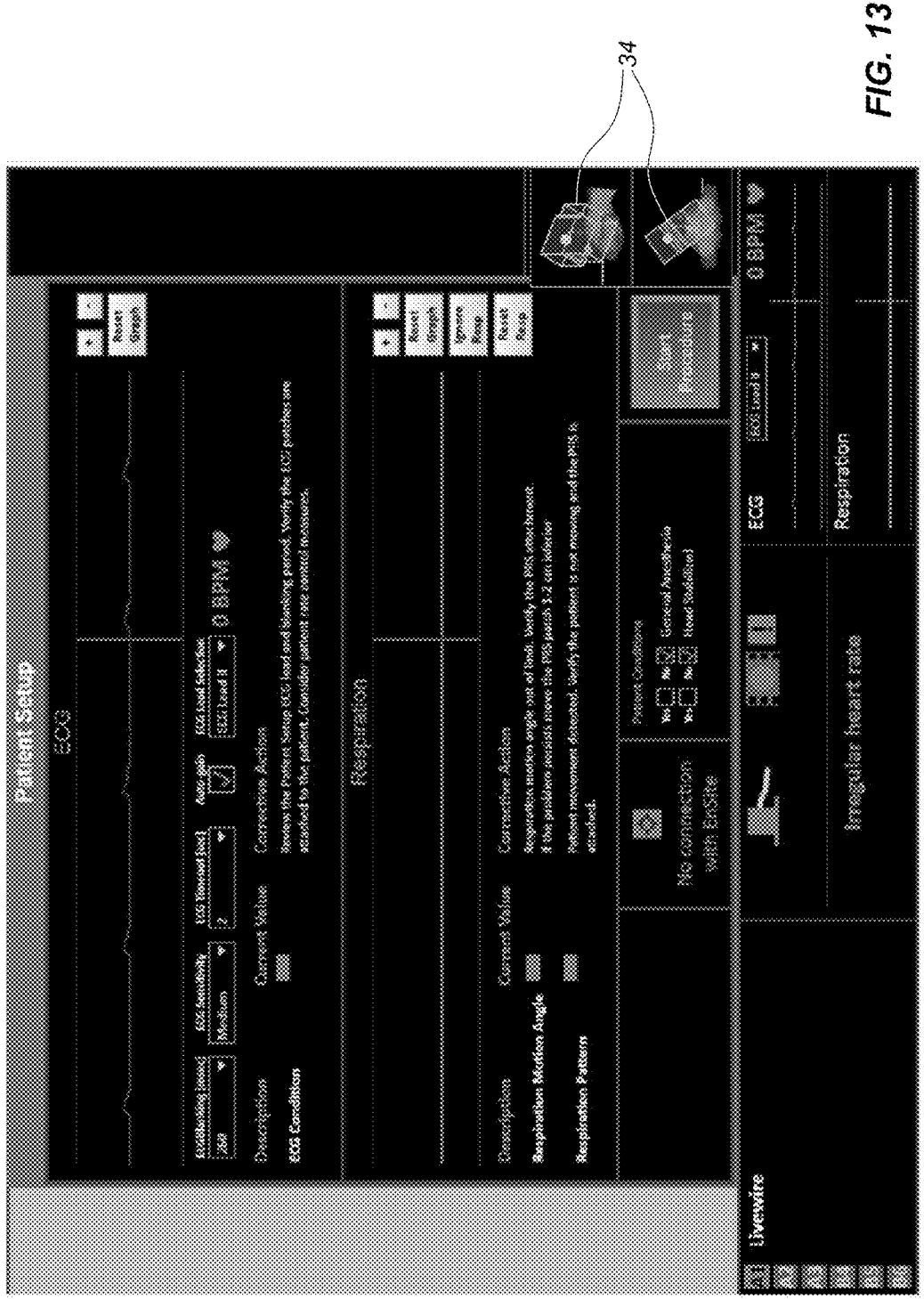

FIG. 13 is an image depicting the visualization of a motion box, a patient reference sensor, medical device sensor(s), and a thorax in reference to a table coordinate system alongside additional information relevant to a medical procedure.

Figure 1:
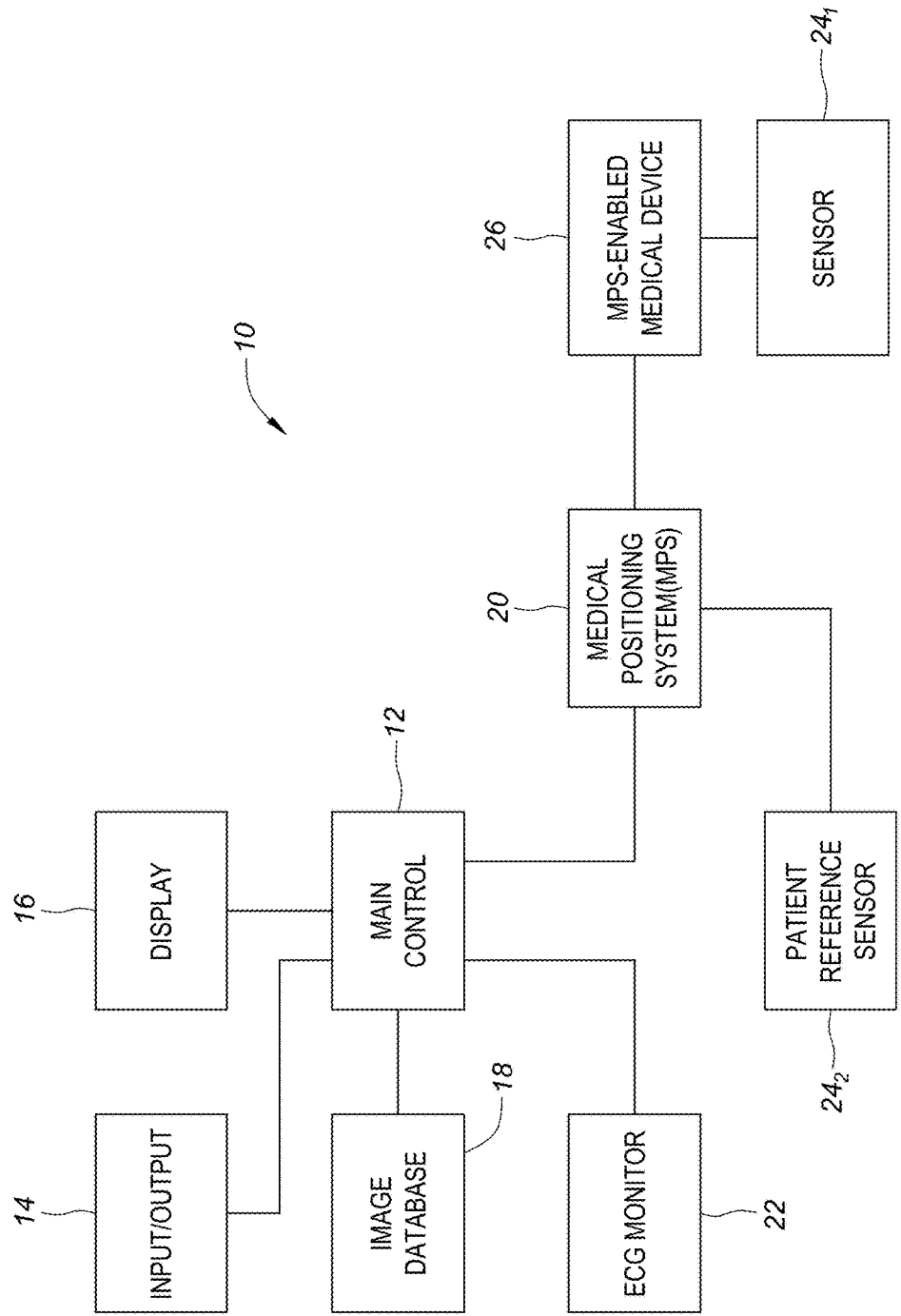
FIG. 1 is a block diagram that schematically represents a system incorporating an embodiment of an electromagnetic sensor tracking system (medical positioning system or MPS) and an MPS-enabled medical device.
Figure 14:
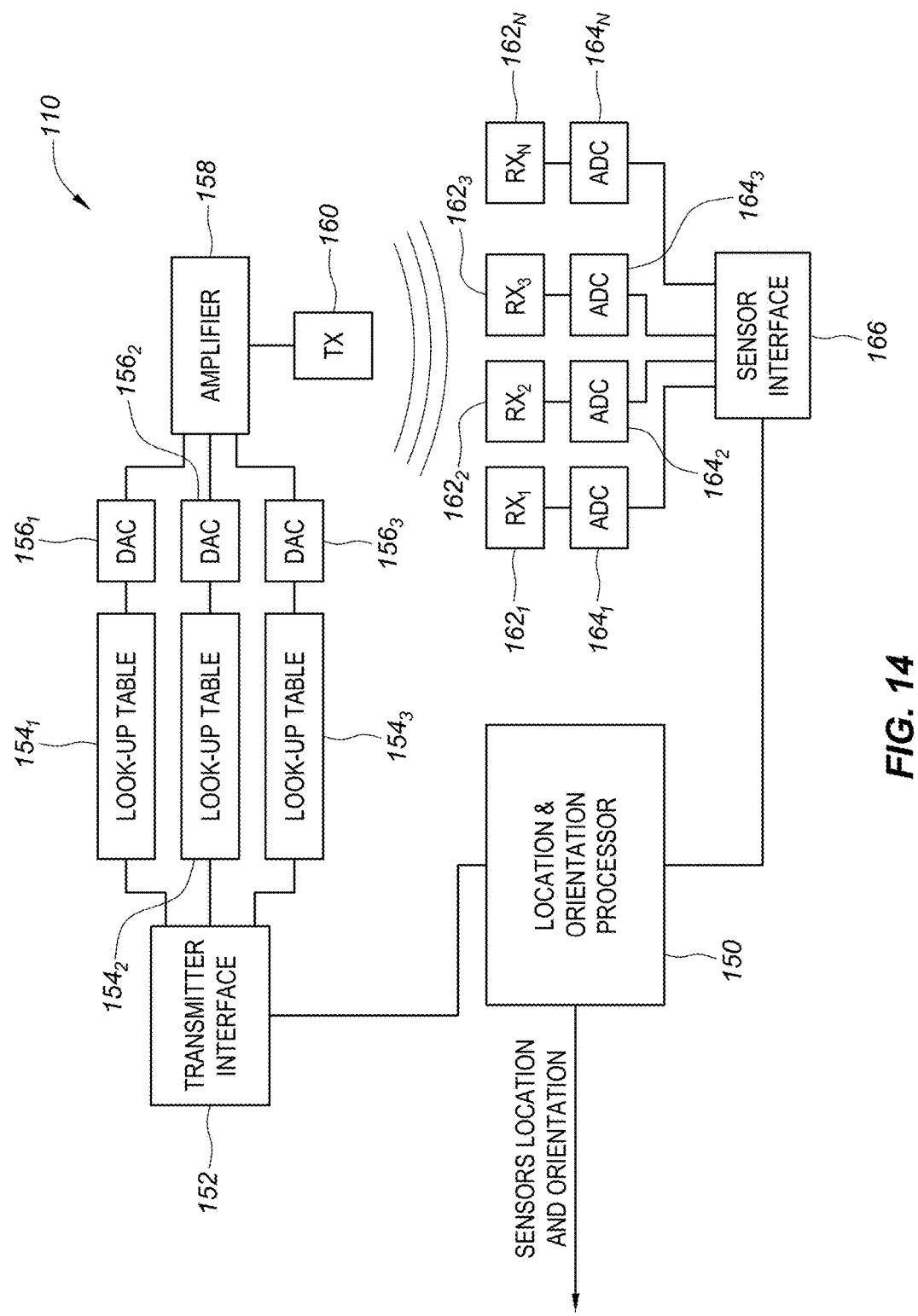

FIG. 14 is a block diagram that schematically represents one exemplary embodiment of a medical positioning system (MPS) as shown in block form in FIG. 1.

DETAILED DESCRIPTION OF EMBODIMENTS

Referring now to the drawings wherein like reference numerals are used to identify identical components in the various views, FIG. 1 is a diagrammatic view of a system 10 in which a position sensing medical device or tool such as a guidewire or catheter may be used. It should be understood that while embodiments will be described in connection with a magnetic field-based positioning system in a catheter-lab environment, this is exemplary only and not limiting in nature.

There is a desire to reduce a patient's exposure to x-rays, such as may be used in live fluoroscopy, at least for the purpose of navigating a medical device such as a catheter within the patient's body. Such a desire may be met by providing a medical device that includes a positioning sensor configured to cooperate with an external (i.e., external to the patient's body) positioning system that can determine the position of the device in three-dimensional space. With this position information, a navigation system can superimpose a representation of the medical device over a previously-obtained image (or series of images) of the region of interest in the patient's body. Additionally, the navigation system can display or visualize a representation of the three-dimensional space in which a magnetic transmitter assembly (MTA) is configured to generate the magnetic field(s) in and around the patient's chest, designated as a motion box, over a previously-obtained image (or series of images) of the region of interest in the patient's body and/or over the representation of the medical device. Accordingly, the clinician may use the superimposed imaging of the medical device and the motion box for navigation purposes rather than using as much fluoroscopy that might otherwise be required. Thus, through the provision of a medical device with position sensing capability and the display of the motion box to aid in the clinician's understanding of the location of the medical device, the use of fluoroscopy (and the accompanying X-ray exposure for the patient) may be reduced significantly. The methods and systems described herein relating to the visualization of the motion box of an electromagnetic medical positioning system (MPS) facilitate the reduction of the need for continuous exposure or extensive use of fluoroscopy for such purposes.

With continued reference to FIG. 1, system 10 as depicted includes a main electronic control unit 12 (e.g., one or more processors) having various input/output mechanisms 14, a display 16, an optional image database 18, a localization system such as a medical positioning system (MPS) 20 (electromagnetic sensor tracking system), an electrocardiogram (ECG) monitor 22, one or more MPS location sensors respectively designated $24_1$ and $24_2$ (i.e., shown as a patient reference sensor), and an MPS-enabled medical device 26 (such as an elongated catheter or introducer) which itself includes one or more of the above-described MPS location sensors, shown in exemplary fashion as having one such sensors $24_1$. In some embodiments, the medical positioning system 20 may comprise a magnetic field-based system such as, for example, the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference.

Input/output mechanisms 14 may comprise conventional apparatus for interfacing with a computer-based control unit, for example, a keyboard, a mouse, a tablet, a foot pedal, a switch or the like. Display 16 may also comprise conventional apparatus.

Embodiments may find use in navigation applications that use imaging of a region of interest. Therefore, system 10 may optionally include image database 18. Image database 18 may be configured to store image information relating to the patient's body, for example, a region of interest surrounding a destination site for medical device 26 and/or multiple regions of interest along a navigation path contemplated to be traversed by device 26 to reach the destination site. The image data in database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL), wherein each image in the sequence has at least an ECG timing parameter associated therewith adequate to allow playback of the sequence in accordance with acquired real-time ECG signals obtained from ECG monitor 22. It should be understood that the foregoing are examples only and not limiting in nature. For example, the image database may also include three-dimensional image data. It should be further understood that the images may be acquired through any imaging modality, now known or hereafter developed, for example X-ray, ultra-sound, computerized tomography, nuclear magnetic resonance or the like.

MPS 20 is configured to serve as the localization system and therefore to determine positioning (localization) data with respect to one or more of MPS location sensors $24_i$ (where i=1 to n) on one or more medical devices 26 and/or on one or more patient reference sensors (PRS) $24_2$ and output a respective location reading. The location readings may each include at least one or both of a position and an orientation (P&O) relative to a reference coordinate system, which may be the coordinate system of MPS 20. For example, the P&O may be expressed as a position (i.e., a coordinate in three axes X, Y, and Z) and orientation (i.e., an azimuth and elevation) of a magnetic field sensor in a magnetic field relative to a magnetic field generator(s) or transmitter(s).

Figure 2:
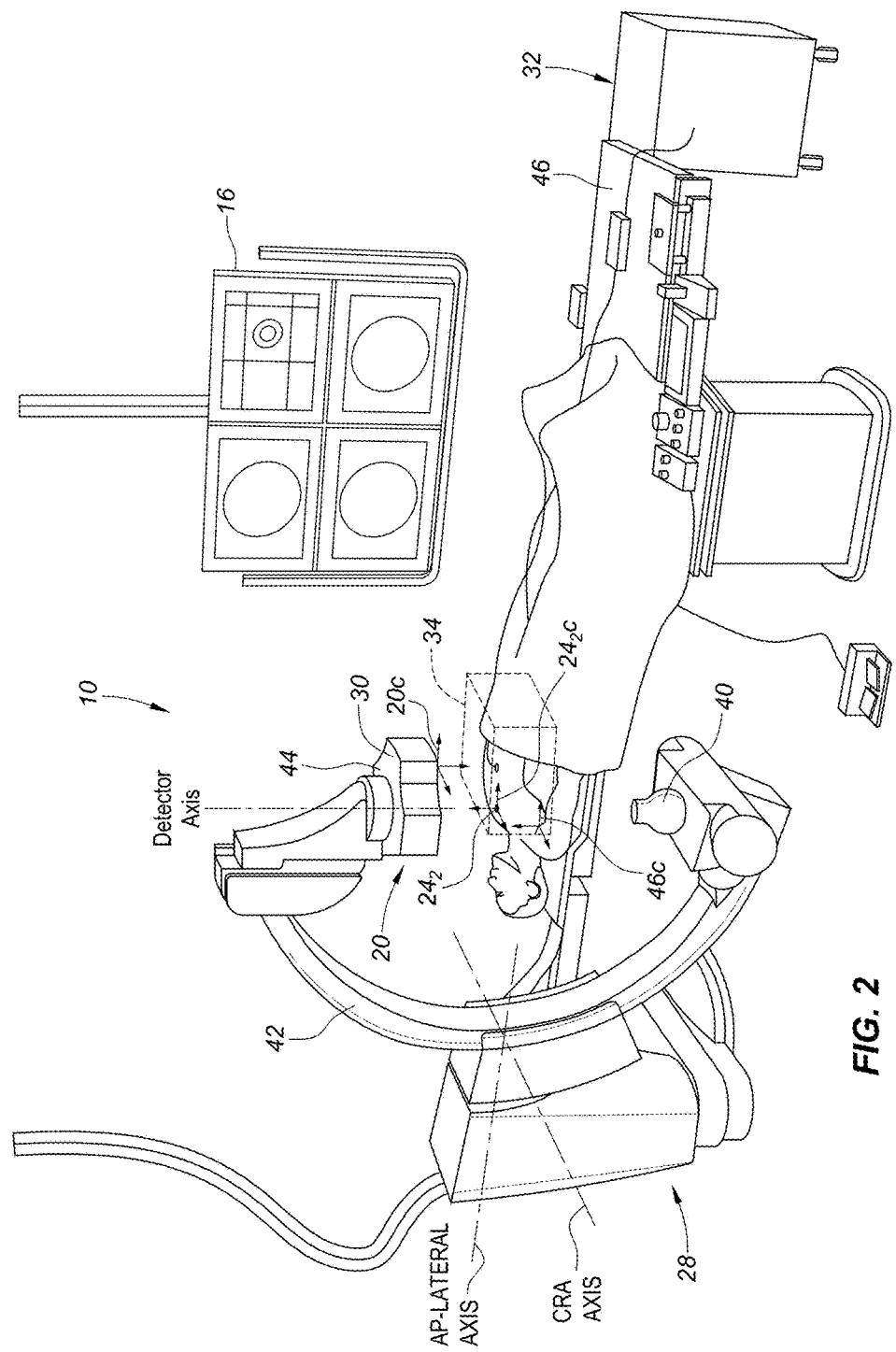
FIG. 2 is a diagrammatic view of the system of FIG. 1 in a catheter-lab environment.

MPS 20 determines respective locations (i.e., P&O) in the reference coordinate system based on capturing and processing signals received from the magnetic field sensors $24_i$ while such sensors are disposed in a controlled low-strength AC magnetic field (see FIG. 2). From an electromagnetic perspective, these sensors develop a voltage that is induced on the coil residing in a changing magnetic field, as contemplated here. Sensors $24_i$ are thus configured to detect one or more characteristics of the magnetic field(s) in which they are disposed and to generate an indicative signal, which is further processed by MPS 20 to obtain a respective P&O of the sensors. Exemplary design features and manufacturing processes and methods for sensors $24_i$ and medical devices incorporating such sensors may be found in U.S. Pat. No. 8,636,718, the entirety of which is incorporated by reference herein.

MPS sensor $24_1$, and optionally additional MPS sensors in further embodiments, may be associated with MPS-enabled medical device 26. Another MPS sensor, namely, patient reference sensor (PRS) $24_2$ (see FIGS. 1 and 2) is configured to provide a positional reference of the patient's body so as to allow motion compensation for gross patient body movements and/or respiration-induced movements. PRS $24_2$ may be attached to the patient's manubrium sternum, a stable place on the chest, or another location that is relatively positionally stable. Like MPS location sensor $24_1$, PRS $24_2$ is configured to detect one or more characteristics of the magnetic field in which it is disposed wherein MPS 20 provides a location reading (e.g., a P&O reading) indicative of the PRS's position and orientation in the reference coordinate system.

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit 12 for ECG synchronized playback of a previously captured sequence of images (cine loop) stored in database 18. The ECG monitor 22 and the ECG-electrodes may both comprise conventional components.

Figure 3:
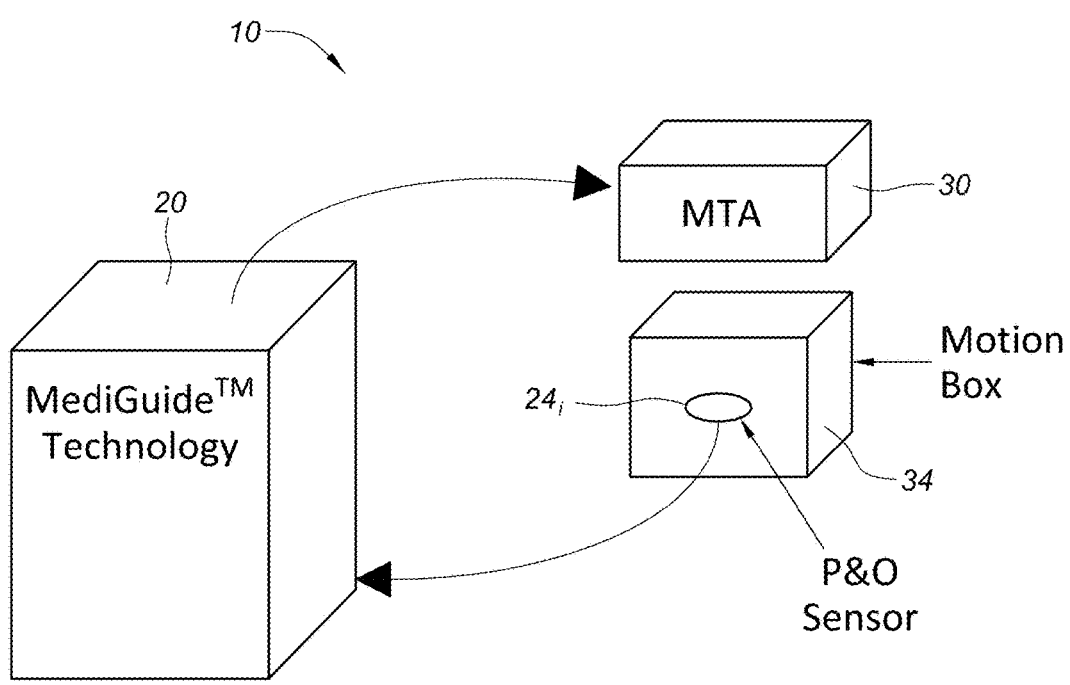
FIG. 3 is a block diagram of the system of FIG. 1 in a catheter-lab environment.

FIG. 2 is a diagrammatic view of the system 10 as incorporated into an exemplary catheter laboratory, and FIG. 3 is a block diagram of the system 10. The system 10 is shown as being incorporated into or associated with a fluoroscopic imaging system 28, which may include commercially available fluoroscopic imaging components, for example, an x-ray source 40, a C-Arm 42, and/or an x-ray image intensifier or detector 44 (i.e., "Catheter Lab"). MPS 20 (electromagnetic sensor tracking system) includes a magnetic transmitter assembly (MTA) 30 (electromagnetic field generator) and a magnetic processing core 32 for determining location (P&O) readings. MTA 30 is configured to generate the magnetic field(s) in and around the patient's chest cavity, in a predefined three-dimensional space identified as a motion box 34. MPS sensors $24_i$ are, as described above, configured to sense one or more characteristics of the magnetic field(s) when the sensors are in motion box 34, and each generate a respective signal that is provided to magnetic processing core 32. Processing core 32 is responsive to these detected signals and is configured to calculate respective P&O readings for each MPS sensor $24_i$ in motion box 34, processing core 32 can detect when an MPS sensor $24_i$ exits the motion box 34. Thus, MPS 20 enables real-time tracking of each sensor $24_i$ in three-dimensional space. The actual volume of motion box 34 may be stored in, for example, processing core 32, and processing core 32 is able to determine the positions and orientations of each sensor $24_i$ in relation to the boundaries of motion box 34. Alternatively, the actual volume of motion box 34 may be stored in, for example, main control 12, and main control 12 may be able to determine the positions and orientations of each sensor $24_i$ in relation to the boundaries of motion box 34. Accordingly, the system can evaluate (e.g., in the processing core or in the main control) whether a sensor $24_i$ is within, at the boundary of, or outside of motion box 34. Based on this information, motion box 34 and sensor(s) $24_i$ can be displayed in relation to one another on display 16 as described in greater detail elsewhere herein.

In some alternative embodiments, as shown in FIG. 4, MTA 30' can be located underneath a patient examination table 46, between an x-ray source 40 and the patient examination table 46. For example, MTA 30' can be connected with the patient examination table 46. In some embodiments, as discussed herein, the MTA can be a mobile device, which can be placed on a chest of the patient and used to generate the magnetic field for tracking of the object.

The positional relationship between the image coordinate system and the MPS reference coordinate system (electromagnetic tracking coordinate system) may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in database 18), a registration step registering the MPS coordinate system and the image coordinate system may need to be performed so that MPS location readings can be properly coordinated with any particular image being used.

Figure 5A:
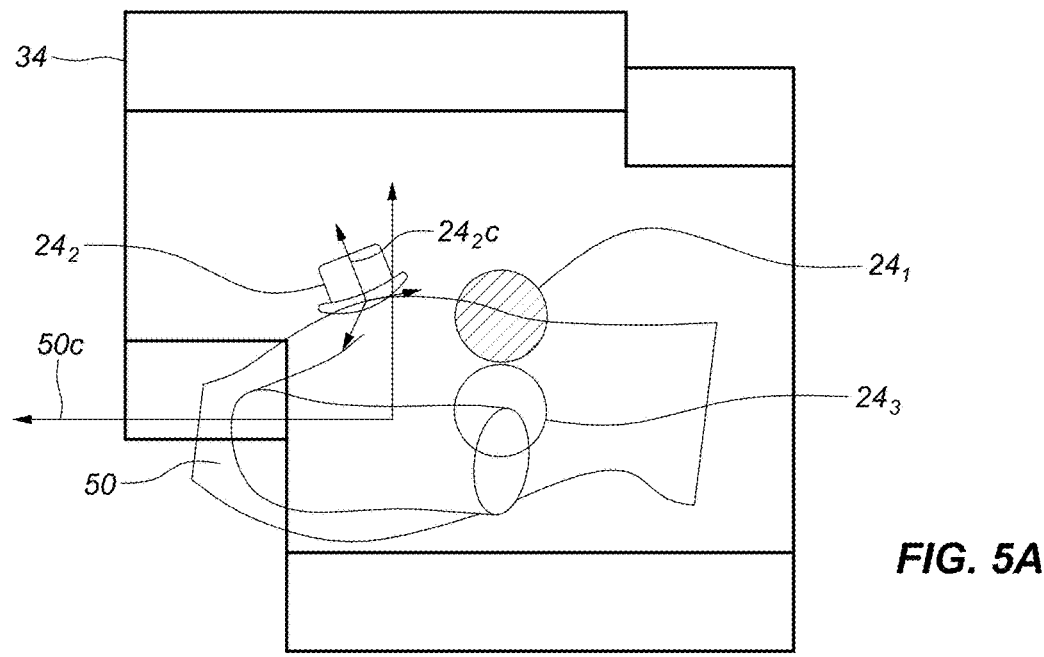
FIGS. 5A and 5B are images depicting the visualization of a motion box, a patient reference sensor, medical device sensor(s), and a thorax in reference to a table coordinate system.
Figure 5B:
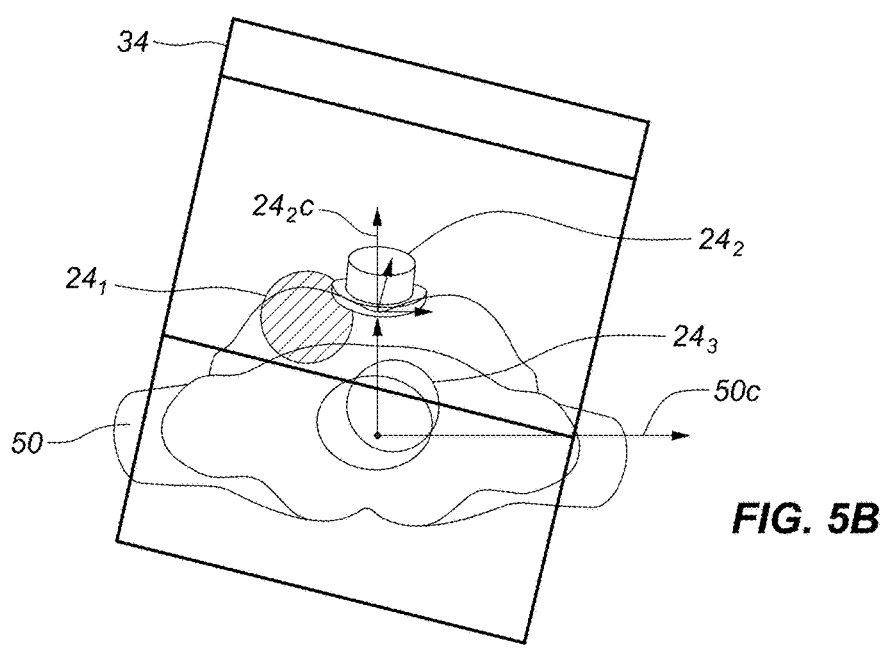

FIG. 5A is a representation of the visualization or display of the position and orientation (P&O) of each sensor $24_i$ and motion box 34 with respect to a representation of the patient's thorax 50 from the right/left (RL) view, and FIG. 5B is a visualization or display of the position and orientation of each sensor $24_i$ and motion box 34 with respect to a representation of thorax 50 from the caudal/cranial (CRA) view. The display of each sensor $24_i$ may be associated with, for example, the patient reference sensor (PRS) $24_2$, and sensors $24_1$, $24_3$ on different medical devices 26. Specifically the position and orientation of each sensor $24_i$ and the position and orientation (P&O) of motion box 34 may be displayed on display 16. Furthermore, the representation of each sensor $24_i$ includes a visual indicia (e.g., color, shape, shading, hatching, stippling, etc.) so that the clinician can distinguish between each sensor $24_i$. For example only, patient reference sensor $24_2$ may be displayed on display 16 as having a "top hat" shape and may be green in color (shown as having a "top hat" shape and white in color), sensor $24_1$ may be displayed on display 16 as having a spherical shape and may be red in color (shown as having a spherical shape and cross-hatched), sensor $24_3$ may be displayed on display 16 as having a spherical shape and may be yellow in color (shown as having a spherical shape and white in color). It will be understood that the clinician may select from a variety of visual indicia including color and/or shape. For example, if a non-spherical shape is selected for each sensor $24_i$, the orientation of each sensor $24_i$ may be easily displayed on display 16.

The representation of the thorax 50, which schematically depicts the orientation of the patient to help orient the clinician, is provided for aiding the display of the orientation of motion box 34 and sensors $24_i$. As described above, patient reference sensor $24_2$ is generally attached to the patient's manubrium sternum. Accordingly, the thorax 50 is generally shown on display 16 such that the sternum of thorax 50 coincides with the displayed location of patient reference sensor $24_2$. Thus, the displayed sternum of thorax 50 and the displayed patient reference sensor $24_2$ may be touching and/or the displayed patient reference sensor $24_2$ may be shown as partially or completely intersecting with the displayed sternum of thorax 50. Thus, as shown in FIGS. 5A and 5B, the origin of the patient reference sensor coordinate system $24_2c$ is coincident with the sternum of the thorax 50. Alternatively, if patient reference sensor $24_2$ is attached at another location on the patient, such as for example, a stable place on the chest, or another location that is relatively positionally stable, then that corresponding position on the thorax 50 may be shown on display 16 as coinciding with the displayed location of patient reference sensor $24_2$. The position of the thorax 50 will be displayed on display 16 such that the displayed position of the patient reference sensor $24_2$ on the thorax 50 matches the position of the patient reference sensor $24_2$ on the patient. Stated yet another way, the thorax 50 includes a depiction of a location corresponding to the location of patient reference sensor $24_2$ on the patient, and thorax 50 is displayed on display 16 in a position such that the location on thorax 50 corresponding to the location of patient reference sensor $24_2$ on the patient is coincident with the displayed transformed position of patient reference sensor $24_2$. Additionally, the thorax 50 is displayed such that the orientation of the thorax coordinate system $50c$ (see FIGS. 5A and 5B) is parallel to the table coordinate system $46c$ (see FIG. 2) (with the axes of the thorax coordinate system $50c$ parallel to the axes of the table coordinate system $46c$). As described in greater detail below, table coordinate system $46c$ (see FIG. 2) is a virtual coordinate system used by system 10 to orient and produce the representation of the motion box 34, thorax 50, patient reference sensor $24_2$, and any sensors $24_i$ as shown on display 16. Table coordinate system $46c$ is always aligned with the physical environments where the clinician operates (i.e., the axes of the table coordinate system $46c$ are always parallel to the edges of the table 46). Thus, table coordinate system $46c$ is used by the software in system 10 to present a representation of the motion box 34, thorax 50, patient reference sensor $24_2$, and any sensors $24_i$ to aid a clinician in understanding where the motion box 34 is in physical space in relation to the patient, patient reference sensor $24_2$, and any sensors $24_i$.

Figure 5C:
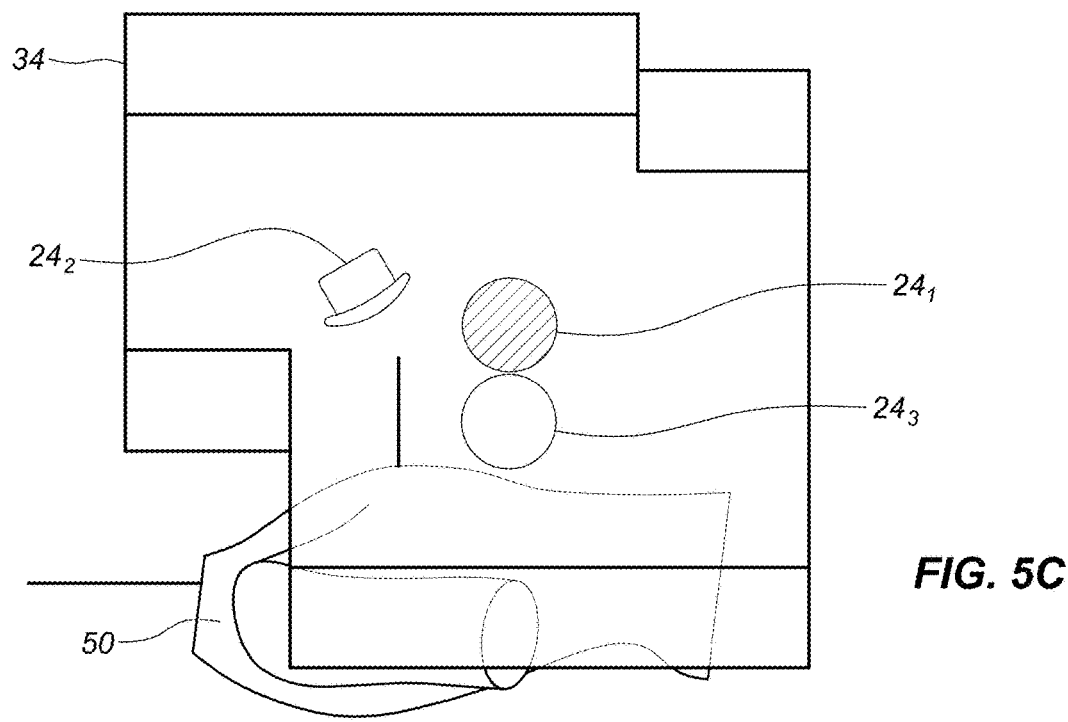
FIGS. 5C and 5D are images depicting the visualization of a motion box, a patient reference sensor, medical device sensor(s), and a thorax in reference to a table coordinate system.
Figure 5D:
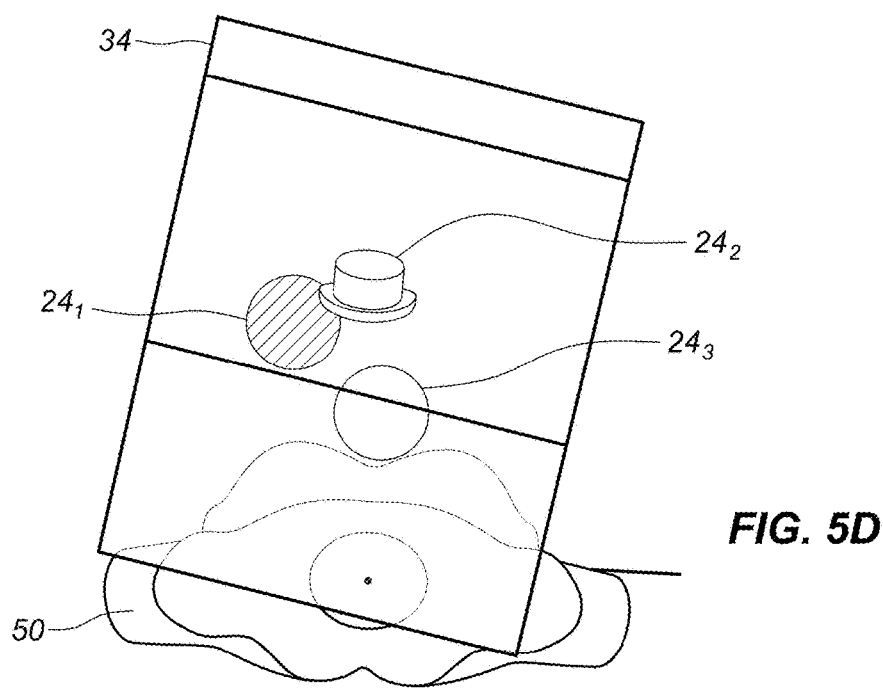

While generally only the measured position of patient reference sensor $24_2$ is used to locate the displayed position of thorax 50, it will be understood that in some embodiments, for example only and without limitation, that the measured orientation of patient reference sensor $24_2$ will also be used to orient the displayed position of thorax 50. Therefore, the position and orientation of the displayed thorax 50 may be based on the measured position and orientation of the patient reference sensor $24_2$. In such embodiments, the thorax coordinate system $50c$ may not be parallel to the table coordinate system $46c$. In other embodiments, for example only and without limitation, the displayed position and orientation of thorax 50 may be refined by affixing additional patient reference sensors to the patient. With reference to FIGS. 5C and 5D, in yet other embodiments, for example only and without limitation, the displayed position of the displayed thorax 50 may not coincide with the measured position of the patient reference sensor $24_2$. That is, in such embodiments, thorax 50 is not representative of the actual physical location of the patient and sensors $24_1$, $24_2$, and $24_3$ may be shown as floating above thorax 50 even though such sensors are on and/or in the patient. In yet other embodiments, the clinician can select where patient reference sensor $24_2$ is located on the thorax 50 displayed on display 16. That is, using a mouse, a finger, stylus or some other input device, the clinician can click on a location of the displayed thorax 50 where the patient reference sensor $24_2$ is actually located on the patient so that system 10 knows where to align the displayed thorax 50 with the patient reference sensor $24_2$ displayed on display 16. For example, if the patient reference sensor $24_2$ is located near a kidney of the patient, the clinician can click on the displayed thorax 50 at or near the same location on the displayed thorax 50 as the patient reference sensor $24_2$ near the kidney of the patient. This allows alignment or co-registration of the displayed virtual space with the actual patient space.

In some embodiments, system 10 may not use a fixed table coordinate system $46c$ or a thorax coordinate system $50c$. In such embodiments, only a patient coordinate system as measured, for example only and without limitation, by one or more patient reference sensors $24_2$, may be used for computation of the motion box 34 visualization with respect to the magnetic coordinate system $20c$.

Figure 6:
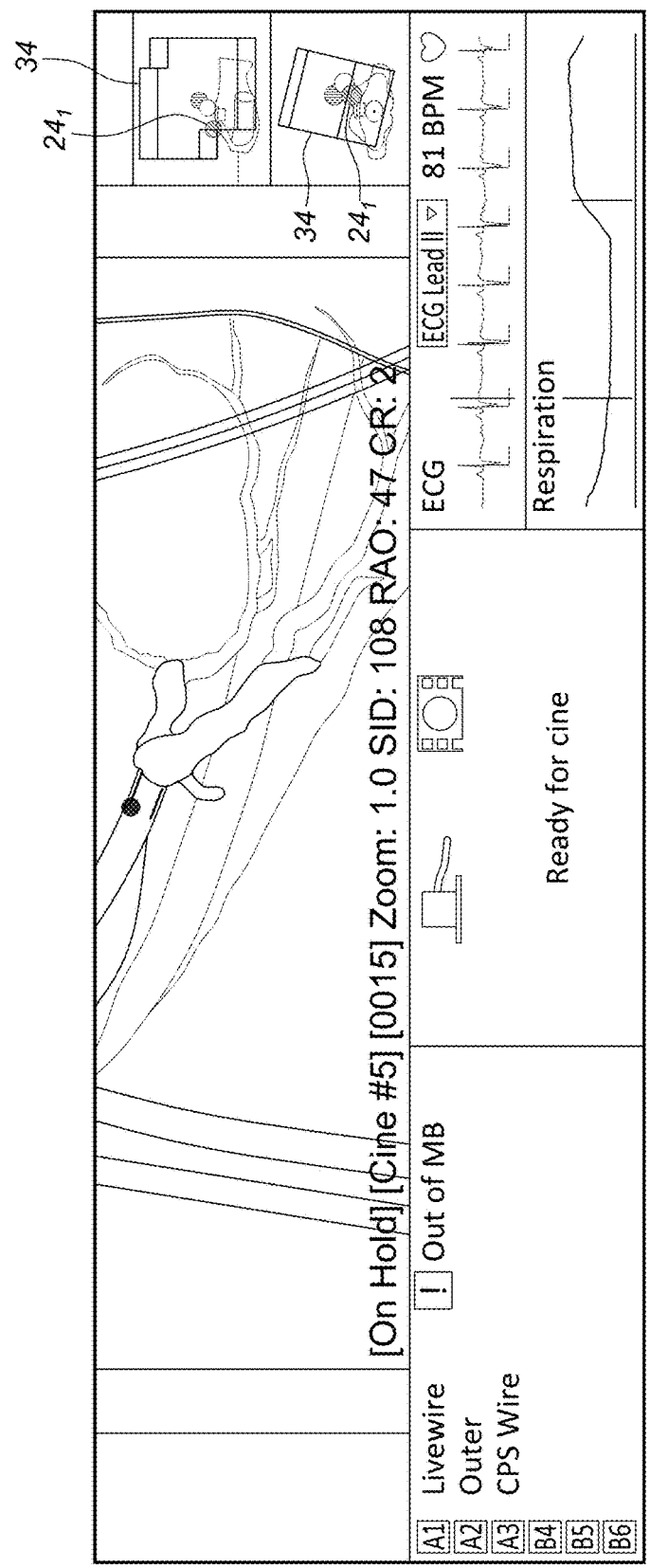
FIG. 6 is an image depicting the visualization of a motion box, a patient reference sensor, medical device sensor(s), and a thorax in reference to a table coordinate system alongside additional information relevant to a medical procedure.
Figure 7:
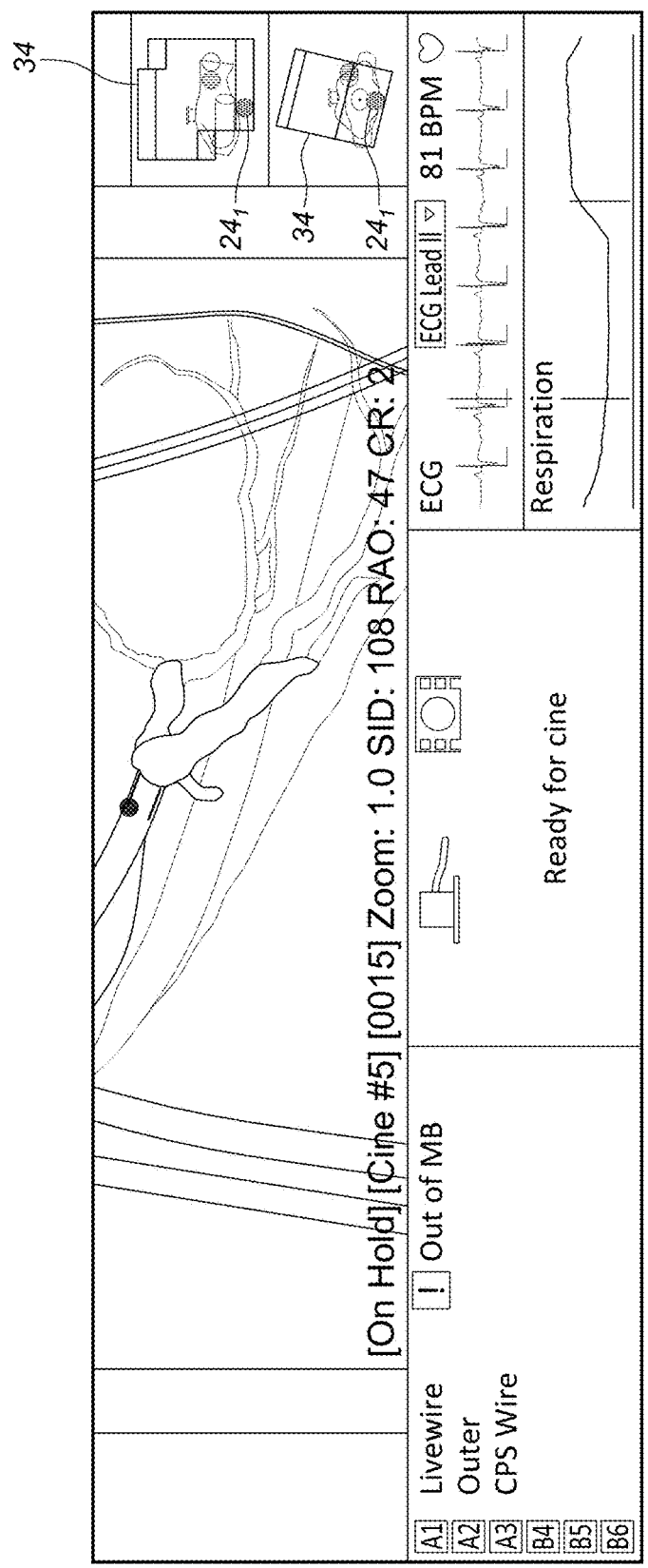
FIG. 7 is an image depicting the visualization of a motion box, a patient reference sensor, medical device sensor(s), and a thorax in reference to a table coordinate system alongside additional information relevant to a medical procedure.

While sensors $24_i$ are within motion box, they are shown in their measured P&O with their selected indicia. However, as shown in FIG. 6, in at least some embodiments, when a sensor $24_i$ of medical device exits motion box 34, the sensor $24_i$ will be represented at the edge of motion box 34 graphic boundary at the point where it exited (see $24_1$) and the device status "Out of MB," or some other appropriate status identifier, will be shown on display 16. Furthermore, when a sensor $24_i$ of a medical device exits motion box 34, but at a distance less than some margin-distance from the boundary of motion box 34 and MPS 20 still reports valid measurements of P&O of sensor $24_i$, the current P&O (and not the last position within motion box 34) may be displayed on display 16. Generally, in various embodiments, for example only and without limitation, the margin distance is about 1.0 cm. However, in some embodiments, for example only and without limitation, the margin distance may be about 0.5 cm to about 3.0 cm (e.g., about 0.5 cm, about 1.0 cm, about 1.5 cm, about 2.0 cm, about 2.5 cm, about 3.0 cm). In the case where an invalid P&O of sensor $24_i$ is determined by MPS 20, such that the actual position of sensor $24_i$ is unknown, the device status "Out of MB," or some other appropriate status identifier, will be shown on display 16 and sensor $24_i$ will be represented at the bottom of motion box 34, and its selected indicia will be altered to an indicia representing an error. For example, as shown in FIG. 7, sensor $24_1$ previously displayed in red (shown as having a spherical shape and cross-hatched in FIGS. 5A and 5B) will be displayed in amber (shown as having a spherical shape and dotted) at the bottom of motion box 34.

As referenced above, the P&O of motion box 34 may be represented on display 16. In various embodiments, MTA 30 is fixed to C-Arm 42. Due to the fixation of MTA 30 to C-Arm 42, MTA 30 rotates and/or translates together with C-Arm 42. Therefore, if C-Arm 42 is rotated in either the caudal/cranial, right/left, and/or detector axes, and/or C-Arm 42 translates in x, y, z directions with respect to the room, MTA 30 and motion box 34 will move accordingly. Thus as shown in FIG. 5B, motion box 34 is represented at a slight angle with respect to the patient's torso. With reference again to FIG. 2, MPS 20 has an MPS coordinate system $20c$ (electromagnetic tracking coordinate system) and because MTA 30 is fixed to C-Arm 42, MPS coordinate system $20c$ moves in relation to the coordinate system of the C-Arm 42. As such, in various embodiments, registration of MPS coordinate system $20c$ to the coordinate system of the C-Arm 42 is not required. Because C-Arm 42 and MTA 30 move in relation to table 46, MPS coordinate system $20c$ moves in relation to table coordinate system $46c$. Therefore, as described in greater detail elsewhere herein, an MPS coordinate system $20c$ to table coordinate system $46c$ transformation matrix must be calculated to transform the positions and orientations of motion box 34, sensors 24$_i$, and thorax 50 measured in the MPS coordinate system 20c to the table coordinate system 46c so that motion box 34, sensors 24i, and thorax 50 can be properly displayed in relation to one another on display 16.

Figure 8A:
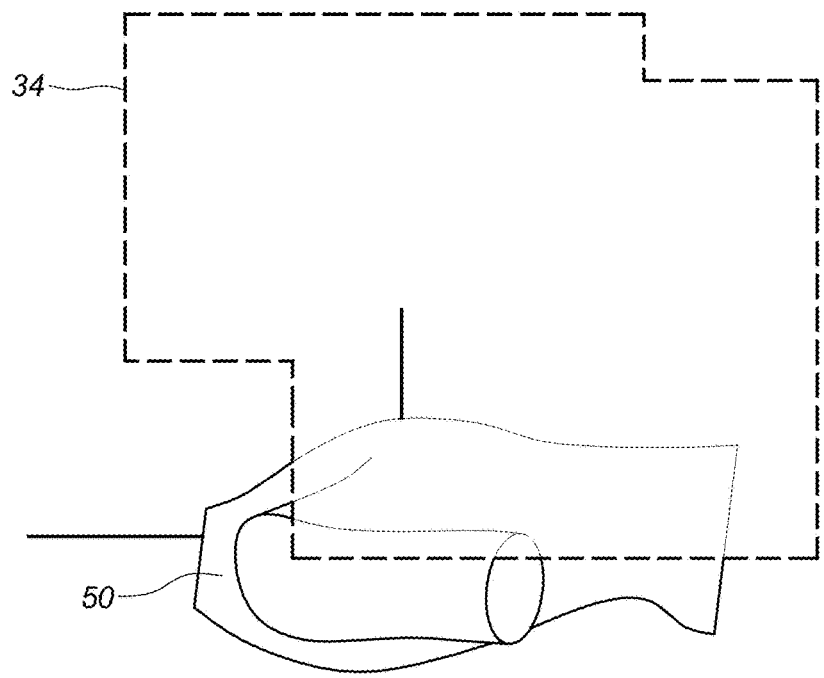
FIGS. 8A and 8B are images depicting the visualization of a motion box, a patient reference sensor, medical device sensor(s), and a thorax in reference to a table coordinate system when the system is unable to accurately determine the location of one or more medical device sensors.
Figure 8B:
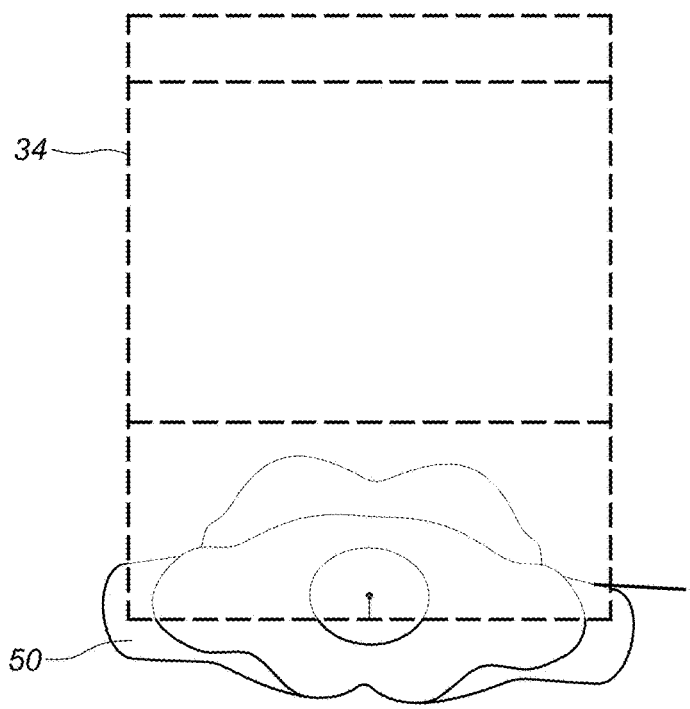

The representation of motion box 34 further includes a visual indicia to indicate information regarding motion box 34. For example, when patient reference sensor 24$_2$ is connected to system 10 and system 10 is in an operable state, motion box 34 is shown with green lines indicating the boundaries of motion box 34 and is shaded green (shown as solid lines in FIGS. 5A and 5B). Conversely, if system 10 determines that there is an error state, the representation of motion box 34 may be altered to include a visual indicia to indicate such error state. For example, when patient reference sensor 24$_2$ or medical device sensor sensors (e.g., 24$_1$, 24$_3$) are not connected to system 10, patient reference sensor 24$_2$'s position and orientation is unknown, or system 10 is in an inoperable state, motion box 34 is shown with amber lines indicating the boundaries of motion box 34 and is shaded amber (shown as dashed lines in FIGS. 8A and 8B) and the disconnected patient reference sensor 24$_2$ or medical device sensor sensors (e.g., 24$_1$, 24$_3$) will not be shown on display 16. Of course, other colors, line styles (e.g., dashed, dotted) or shading could be used to indicate this status information. Additionally, as shown in FIGS. 8A and 8B, the displayed motion box 34 may be shown in a substantially vertical up-and-down orientation. This may occur, for example only and without limitation, where the C-Arm 42 with integrated MTA 30 is not angulated with respect to the table 46 (i.e., non-zero angle with respect to the table 46). In other embodiments, for example only and without limitation, motion box 34 may be shown in a substantially vertical up-and-down orientation when the MTA 30' is fixed to the table 46 and cannot move in relation to the table 46 (see FIG. 4).

During a procedure performed by a clinician, one or more medical devices, each having one or more sensors 24$_i$ are inserted into and/or are navigated within patient. At times during the procedure, one or more of the medical devices may go out of the electromagnetic field generated by MTA 30, and thus exit motion box 34. Without the representation of motion box 34, sensors 24$_i$, and the environment in which the clinician operates system 10 (such as the patient's thorax in the case of usage of system 10 during medical procedures), the ability of the clinician to bring the medical devices and associated sensors 24$_i$ back into the electromagnetic field generated by MTA 30 may be hindered. Accordingly, in existing systems, where there is no representation of motion box 34 to the clinician, the clinician may lose one or more sensors 24$_i$ and it may be time consuming and/or difficult for the clinician to navigate the one or more sensors 24i back into the motion box 34. This may result in the addition of unnecessary, and potentially harmful, time to the procedure. Furthermore, the loss of location awareness of one or more of sensors 24$_i$ may force the clinician to take additional fluoroscopic images to find the one or more medical devices. This subjects the patient, as well as the clinicians present in the Catheter Lab, to additional radiation. Therefore, the superimposition of a representation of sensors 24$_i$, motion box 34, and thorax 50 on display 16, as provided by system 10, aids a clinician in maintaining the medical devices within motion box 34, and may reduce the time and/or number of additional fluoroscopic images it takes to return a medical device to motion box 34, in the event the medical device exits motion box 34.

Figure 9:
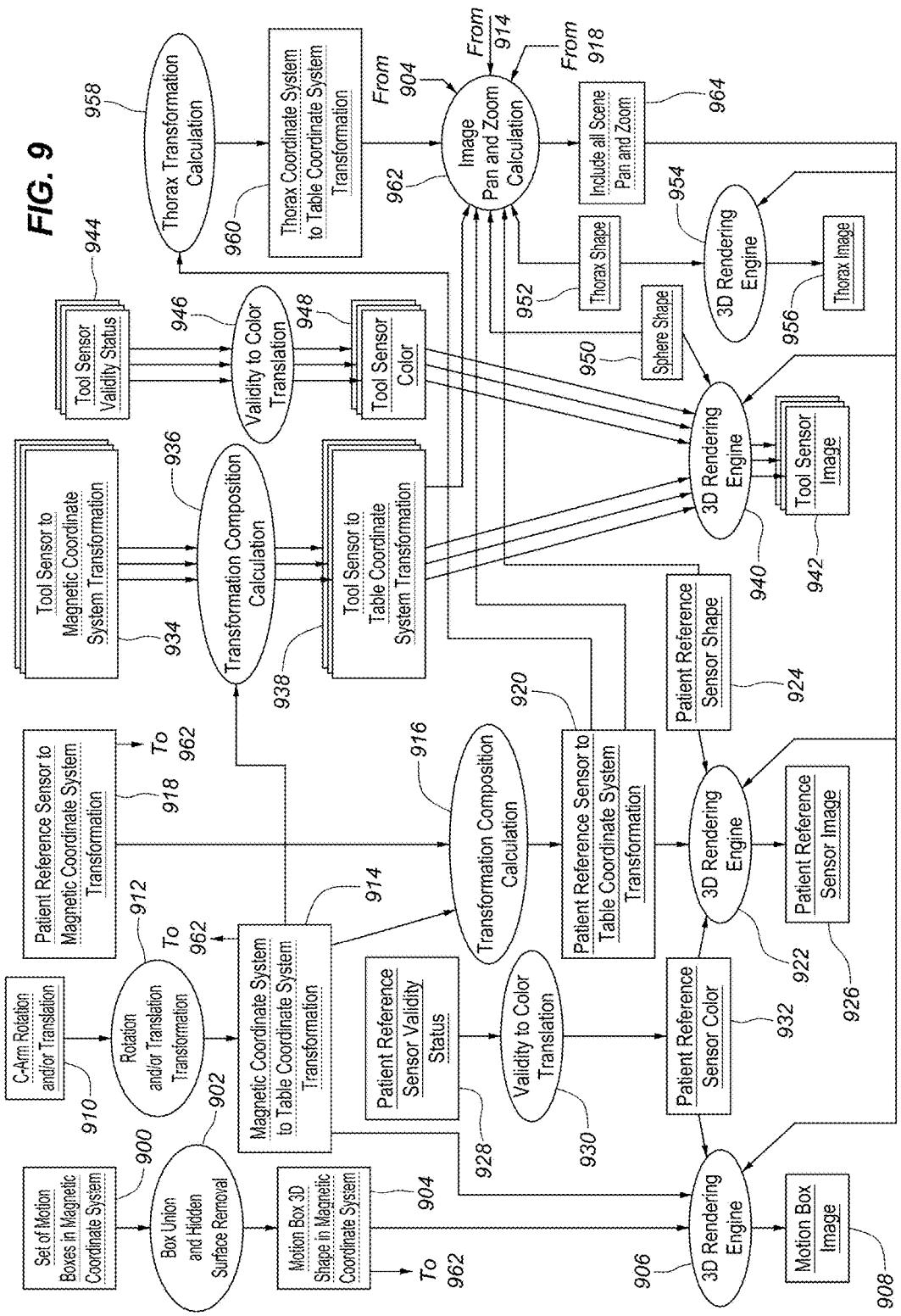
FIG. 9 is flowchart of the method of visualizing a motion box, a patient reference sensor, medical device sensor(s), and a thorax in reference to a table coordinate system.

FIG. 9 is a flowchart of a method of operating system 10 and visualizing a representation of motion box 34 on a display 16. First, the steps of calculating the relative transformation of motion box 34, sensors 24$_i$, and the thorax 50 will be described. Second, the steps of rendering motion box 34, sensors 24$_i$, and the thorax 50 will be described. With respect to the method described herein, it is assumed that the MPS 20 operates in system 10 as incorporated into a fluoroscopic imaging system 28 or Catheter Lab environment and that the rotation angles, translations in x, y, z directions with respect to the room, and SID (source-intensifier-distance) of C-Arm 42 and/or the translations of table 46 in x, y, z directions with respect to the room may be available and input into MPS 20. It is also assumed that MTA 30 is affixed to C-Arm 42, such that when C-Arm 42 rotates and/or translates, the MPS coordinate system 20c rotates and/or translates together with C-Arm 42. Furthermore, table coordinate system 46c is set as a static coordinate system parallel to table 46 and system 10 calculates spatial transformations of the thorax 50, motion box 34, and sensors 24$_i$ relative to table coordinate system 46c. That is, table coordinate system 46c is a virtual coordinate system used by system 10 to orient and produce the representation of the motion box 34, thorax 50, patient reference sensor 24$_2$, and any sensors 24$_i$ as shown on display 16. Table coordinate system 46c is used by the software in system 10 to present a representation of the motion box 34, thorax 50, patient reference sensor 24$_2$, and any sensors 24$_i$ to aid a clinician in understanding where the motion box 34 is in physical space in relation to the patient, patient reference sensor 24$_2$, and any sensors 24$_i$.

Calculating Relative Spatial Transformation of Motion Box 34, Sensors 24$_i$, and Thorax 50

Blocks 900 and 902 correspond to the construction of motion box 34 in MPS 20 coordinate system. As can be seen in FIGS. 5A, 5B, 8A, and 8B, motion box 34 is not a cube, but may be an irregular cuboid or parallelepiped shape which represents a volume of physical space in which the electromagnetic field generator or magnetic transmitter assembly 30 generates a magnetic field for measuring the position and/or orientation of medical device sensors 24$_i$. That is, motion box 34 represents the spatial region in which a voltage may be induced in medical device sensors 24$_i$ by the electromagnetic field generator or magnetic transmitter assembly 30. At block 902, the motion boxes that form motion box 34 are joined and any hidden surfaces are removed. What results is the three-dimensional shape of motion box 34 in MPS 20 coordinate system at block 904.

At blocks 910 and 912, system 10 determines the position of C-Arm 42 with respect to the table coordinate system 46c by measuring a first rotation of C-Arm 42 around a caudal/cranial axis and a second rotation of C-Arm 42 around a AP-lateral (left/right) axis, to determine the rotation and translation of the MPS 20 coordinate system relative to the table coordinate system 46c. Thus at block 914, system 10 calculates a MPS coordinate system 20c to a table coordinate system 46c transformation matrix based the measured rotations from blocks 910 and 912. This MPS coordinate system 20c to table coordinate system 46c transformation matrix is then used throughout the method to transform the P&O of the patient reference sensor 24$_2$, any medical device sensors 24$_1$, and motion box 34 into the table coordinate system 46c for display to a clinician on display 16. Thus, as described in greater detail below, the MPS coordinate system 20c to table coordinate system 46c transformation matrix from block 914 is input into blocks 906, 916, and 936 to aid in the rendering and display of patient reference sensor $24_2$, any medical device sensors $24_i$, and motion box 34 to the clinician on display 16. Accordingly, motion box 34, thorax 50, patient reference sensor $24_2$, and any sensors $24_i$ that are displayed on display 16 to clinician is rendered in the virtual table coordinate system 46c. Table coordinate system 46c is used by the software in system 10 to present a representation of the motion box 34, thorax 50, patient reference sensor $24_2$, and any sensors $24_i$ to aid a clinician in understanding where the motion box 34 is in physical space in relation to the patient, patient reference sensor $24_2$, and any sensors $24_i$.

In other embodiments, for example only and without limitation, system 10 may a determine the position of the C-Arm with respect to the table coordinate system 46c by measuring one or more of (1) a first rotation of C-Arm 42 around a caudal/cranial axis, (2) a second rotation of C-Arm 42 around a AP-lateral (left/right) axis, (3) a rotation of C-Arm 42 around a vertical (wig wag) axis, (4) a rotation of MTA 30 around the detector axis, (5) translations of C-Arm 42 in the x, y, z directions with respect to the room, (6) translations of the table 46 in the x, y, z directions with respect to the room, and (7) a translation of x-ray image intensifier 44 and MTA 30 either toward or away from x-ray source 40 (e.g., to alter the source-intensifier-distance (SID)) to determine the rotation and translation of the MPS coordinate system 20c relative to the table coordinate system 46c. In other embodiments, table 46 translations and rotations with or without C-Arm 42 rotations and translations may be used to calculate the MPS coordinate system 20c to a table coordinate system 46c transformation matrix.

At block 918, the transformation of the patient reference sensor $24_2$ relative to MPS coordinate system 20c is output from MPS 20. That is, the voltage induced into the patient reference sensor $24_2$ by the magnetic transmitter assembly 30 is transformed into a position and orientation in the MPS coordinate system 20c. Then at block 916, the MPS coordinate system 20c to table coordinate system 46c transformation matrix from block 914 is applied to the result of block 918 to obtain the P&O of the patient reference sensor $24_2$ (PRS) in the table coordinate system 46c at block 920. That is, the patient reference sensor $24_2$ transformation relative to the table coordinate system 46c is calculated at block 916 by applying the transformation composition of the results obtained in blocks 914 and 918.

At block 934, the transformation of the one or more medical device sensors $24_1$, $24_3$ relative to MPS coordinate system 20c is output from MPS 20. That is, the voltage induced into the medical device sensors $24_1$, $24_3$, $24_i$ by the magnetic transmitter assembly 30 is transformed into a position and orientation in the MPS coordinate system 20c. Then at block 936, the MPS coordinate system 20c to table coordinate system 46c transformation matrix from block 914 is applied to the result of block 934 to obtain the P&O of the sensors $24_1$, $24_3$ on each medical device in the table coordinate system 46c at block 938. That is, the medical device sensor $24_1$, $24_3$ transformations relative to the table coordinate system 46c are calculated at block 936 by applying the transformation composition of the results obtained in blocks 914 and 934.

At block 958 the patient reference sensor $24_2$ to table coordinate system 46c transformation from block 920 is applied to calculate the thorax coordinate system 50c to table coordinate system 46c transformation at block 960. The thorax coordinate system 50c (see FIGS. 5A and 5B) is calculated in such a way that its orientation is the same as the orientation of the table coordinate system 46c (see FIG. 2), and its position is such that the part of the thorax 50 shape matching the thorax's sternum is aligned with the patient reference sensor coordinate system $24_2c$ origin. That is, the orientation of the axes of the thorax coordinate system 50c (see FIGS. 5A and 5B) is transformed in block 958 to be parallel to the axes of the table coordinate system 46c (see FIG. 2), resulting in block 960. As described above, when thorax 50 and patient reference sensor $24_2$ are displayed on display 16, the thorax 50 is generally shown such that the sternum of thorax 50 coincides with the displayed location of patient reference sensor $24_2$. Thus, the displayed sternum of thorax 50 and the displayed patient reference sensor $24_2$ may be touching and/or the displayed patient reference sensor $24_2$ may be shown as partially or completely intersecting with the displayed sternum of thorax 50. Stated yet another way, the thorax 50 includes a depiction of a location corresponding to the location of patient reference sensor $24_2$ on the patient, and thorax 50 is displayed on display 16 in a position such that the location on thorax 50 corresponding to the location of patient reference sensor $24_2$ on the patient is coincident with the displayed transformed position of patient reference sensor $24_2$. Thus, the transformation calculation at block 958 and result at block 960 permits for the displayed position of the patient reference sensor $24_2$ on the thorax 50 to match the position of the patient reference sensor $24_2$ on the patient. It will be understood however, that in some embodiments, for example only and without limitation, steps 958 and 960 may be optional or omitted such that the displayed position of the displayed thorax 50 may not coincide with the measured position of the patient reference sensor $24_2$ (see FIGS. 5C and 5D).

At block 962 the image pan and zoom, to be put into the block 964, is calculated. The image pan and zoom ensures that all objects being rendered are fully visible in the resulting image on display 16. The image pan and zoom is calculated from blocks 904 (motion box 34 three-dimensional shape in magnetic coordinate system 20c), 914 (magnetic coordinate system 20c to table coordinate system 46c transformation), 924 (patient reference sensor $24_2$ shape), 918 (patient reference sensor $24_2$ to magnetic coordinate system 20c transformation), 950 (medical device sensors $24_1$, $24_3$, $24_i$ shape), 938 (medical device sensor $24_1$, $24_3$, $24_i$ to table coordinate system transformation 46c, for the number of such transformations as the number of medical device sensors $24_i$ present), 952 (thorax 50 shape), and 960 (thorax coordinate system 50c to table coordinate system 46c transformation).

Image pan and zoom calculation performed by block 962, ensures that all objects to by rendered on display 16, such as motion box 34 (block 904), patient reference sensor $24_2$ (block 924), sensors $24_i$ (block 950), and thorax shape (block 956), are fully visible in the resulting rendered image. The above-mentioned objects are represented in 3D in the table coordinate system.

Figure 9A:
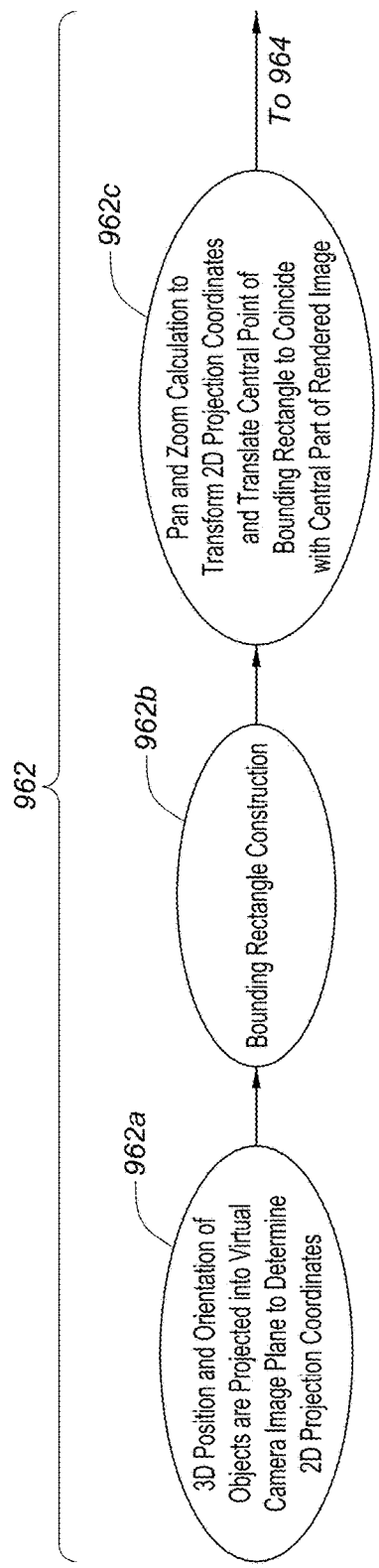
FIG. 9A is flowchart of the method of panning and zooming a visualization of a motion box, a patient reference sensor, medical device sensor(s), and a thorax in reference to a table coordinate system.
Figure 9B:
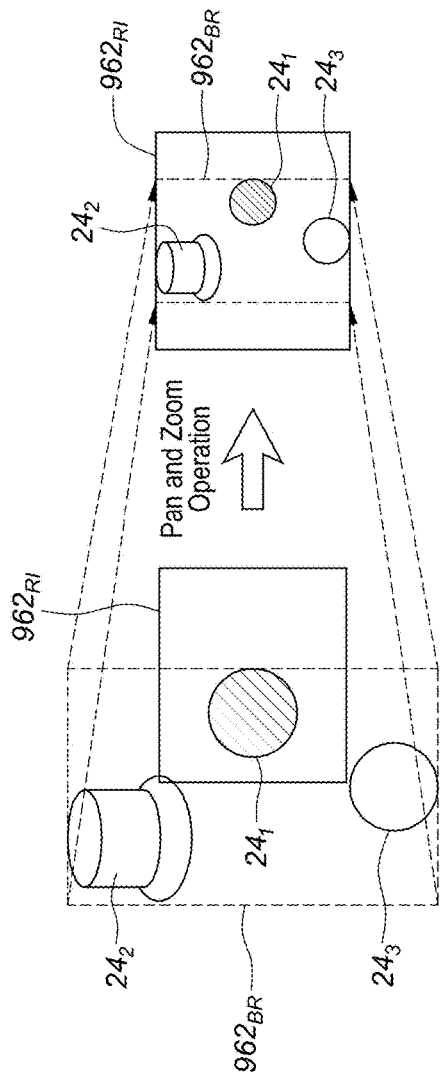

Now with reference to FIGS. 9A and 9B, the steps within block 962 are described. At block 962a, the three-dimensional (3D) positions and orientations of objects (e.g., sensors $24_1$, $24_2$, $24_3$, $24_i$, thorax 50, motion box 34) from blocks 904, 914, 924, 918, 950, 938, 952, and 960 are projected into an image plane of a virtual camera looking at the origin of table coordinate system 46c to determine the projection coordinates, in two-dimensional (2D) space, of the objects (e.g., sensors $24_1$, $24_2$, $24_3$, $24_i$, thorax 50, motion box 34) to be projected into the image plane. The position of the virtual camera may be arbitrary, but if the axes of the virtual camera are parallel to the axes of table coordinate system 46c, front, back, left, right, top or bottom views of the scene may be simulated. Although the virtual camera viewing angle can also be arbitrary, orthographic projection (projection lines are parallel to the viewing direction of the camera) is used.

Then at block 962b, a bounding rectangle $962_{BR}$ of the resulting projection coordinates (in two-dimensional space) is constructed. This bounding rectangle $962_{BR}$ may be bigger or smaller than the visible part of the rendered image which will ultimately be displayed on display 16. Additionally, the aspect ratio of the bounding rectangle $962_{BR}$ may also be different from the aspect ratio of the visible part of the rendered image $962_{RI}$ which will ultimately be displayed on display 16.

At block 962c, the pan and zoom are calculated and applied to the bounding rectangle $962_{BR}$. The pan and zoom calculation ensures that the scene displayed on display 16 is fully visible and as big as possible. The pan and zoom are calculated as two-dimensional transformations and are applied to the two-dimensional projected coordinates of the scene objects (e.g., sensors $24_1$, $24_2$, $24_3$, $24_i$, thorax 50, motion box 34) calculated at block 962a. The calculated pan is a two-dimensional translation transformation that offsets the central point of the scene-projection bounding-rectangle $962_{BR}$ (calculated at block 962a) to coincide with the central point of the visible part of the rendered image $962_m$ on display 16. The calculated zoom is a two-dimensional uniform scale transformation; keeping the aspect ratio of the bounding rectangle $962_{BR}$ and reduces or enlarges it to be fully inside the visible part of the rendered image $962_m$ and as big as possible. The result of block 962 (and blocks 962a, 962b, and 962c, therein) are output to block 964.

Rendering of Motion Box, Sensors $24_i$, and the Thorax 50

Following the transformations of the positions and orientations of each of motion box 34, patient reference sensor $24_2$, and medical device sensors (e.g., $24_1$, $24_3$) from the MPS coordinate system 20c into the table coordinate system 46c as described above, and applying the calculated image pan and zoom, system 10 renders motion box 34, patient reference sensor $24_2$, and medical device sensors $24_1$, $24_3$ for display on display 16 in the appropriate positions and orientations so that a clinician can easily and accurately view motion box 34, patient reference sensor $24_2$, and medical device sensors $24_1$, $24_3$ in relation to one another in the table coordinate system 46c. In various embodiments, main electronic control unit 12 (e.g., one or more processors) of system 10 is adapted to deliver a signal to display 16 to render depictions of motion box 34, patient reference sensor $24_2$, and medical device sensors $24_1$, $24_3$. Motion box 34, patient reference sensor $24_2$, and medical device sensors $24_1$, $24_3$ are displayed on display in two views: right/left (RL) view and caudal/cranial (CRA) view. As described above, sensors $24_1$, $24_3$ of connected medical devices are displayed on display 16 as a sphere having the desired indicia (e.g., color, stippling, cross-hatching, etc.) and patient reference sensor $24_2$ is displayed on display 16 as with an indicia distinguishable from sensors $24_1$, $24_3$ of connected medical devices (e.g., green "top hat" shape).

With continued reference to FIG. 9, the specific rendering steps are described. The rendering and display of motion box 34 is carried out in blocks 906 and 908. At block 906, the MPS coordinate system 20c to table coordinate system 46c transformation matrix from block 914 is applied to the motion box 34 shape from block 904 and input, together with image pan and zoom from block 964, into a 3D rendering engine in main electronic control unit 12. That is, the transformed position and orientation of motion box 34 (block 914), the shape of motion box 34 (block 904) and the rendering zoom or size (block 964) are all fed into 3D rendering engine at block 906 so that the transformed position and orientation and shape of motion box 34 may be appropriately displayed on display 16. At block 908, the 3D rendering engine displays motion box 34 on display 16 with motion box 34 registered to the table coordinate system 46c.

The rendering and display of patient reference sensor $24_2$ is carried out in blocks 920, 928, 930, 932, 922, 926, and 964. Specifically, the result of blocks 920 and 964 are input into the 3D rendering engine at block 922. Additionally, the validity (e.g., connected to system 10, within motion box 34) of the patient reference sensor $24_2$ is determined at block 928. Based on the results of the validity check in block 928, the validity status is changed to an appropriate indicia (e.g., color, stippling, cross-hatching, etc.) at block 930. The appropriate indicia for patient reference sensor $24_2$ is output from block 932 to the 3D rendering engine at block 922, the patient reference sensor $24_2$ shape is output from block 924 to the 3D rendering engine at block 922. That is, the transformed position and orientation information of patient reference sensor $24_2$ (block 920), the validity indicia of patient reference sensor $24_2$ (block 932), the shape of patient reference sensor $24_2$ (block 924), and the rendering zoom or size of patient reference sensor $24_2$ (block 964) are all fed into 3D rendering engine at block 922 so that the transformed position and orientation, validity indicia, shape, and size of patient reference sensor $24_2$ may be appropriately displayed on display 16. At block 926, the 3D rendering engine displays patient reference sensor $24_2$ image on display 16 with patient reference sensor $24_2$ registered to the table coordinate system 46c and superimposed on the visualization of motion box 34.

The rendering and display of each medical device sensor $24_1$, $24_3$ is carried out in blocks 944, 946, 948, 950, 940, 942, and 964. Specifically, the result of blocks 938 and 964 are input into the 3D rendering engine at block 940. Additionally, the validity (e.g., connected to system 10, within motion box 34) of each medical device sensors $24_1$, $24_3$ is determined at block 944. Based on the results of the validity check in block 944, the validity status is changed to an appropriate indicia (e.g., color, stippling, cross-hatching, etc.) at block 946. The appropriate indicia for each medical device sensors $24_1$, $24_3$ is output from block 948 to the 3D rendering engine at block 940, and each medical device sensors $24_1$, $24_3$ shape is output from block 950 to the 3D rendering engine at block 940. That is, the transformed position and orientation information of each medical device sensor $24_1$, $24_3$ (block 938), the validity indicia of each medical device sensor $24_1$, $24_3$ (block 948), the shape of each medical device sensor $24_1$, $24_3$ (block 950), and the rendering zoom or size of each medical device sensor $24_1$, $24_3$ (block 964) are all fed into 3D rendering engine at block 940 so that the transformed position and orientation, validity indicia, shape, and size of each medical device sensor $24_1$, $24_3$ may be appropriately displayed on display 16. At block 942, the 3D rendering engine displays each medical device sensors $24_1$, $24_3$ image on display 16 with each medical device sensor $24_1$, $24_3$ registered to the table coordinate system 46c and superimposed on the visualization of motion box 34.

The rendering and display of thorax 50 is carried out in blocks 952, 954, 956, and 964. Specifically, the thorax 50 shape at block 952 and image pan and zoom at block 964 are output to the 3D rendering engine at block 954. At block 956, the 3D rendering engine displays the thorax 50 image on display 16 with the thorax 50 mage registered to the table coordinate system 46c and superimposed on the visualization of motion box 34.

Accordingly, following the steps described above and the blocks illustrated in FIG. 9, motion box 34 is visualized/displayed on display 16 based on the rotations and/or translations of C-Arm 42 and/or the translations of table 46, and patient reference sensor 24$_2$ and each medical device sensor 24$_1$, 24$_3$ are visualized or displayed on display 16 as described herein based on their positions and orientations and/or status. Thus, while each medical device sensor 24$_1$, 24$_3$ is within motion box 34, blocks 944, 946, 948 and 940, as described above, cause an image (block 942) of each medical device sensor 24$_1$, 24$_3$ to be visualized or displayed on display 16 in their measured positions and orientations with an indicia of a valid status. Additionally, while each patient reference sensor 24$_2$ is within motion box 34, blocks 928, 930, 932 and 922, as described above, cause an image (block 926) of patient reference sensor 24$_2$ to be visualized or displayed on display 16 in its measured position and orientation with an indicia of a valid status.

With reference again to FIG. 6, when a medical device sensor 24$_1$ exits motion box 34, blocks 944, 946, 948 and 940, as described above, cause an image (block 942) of medical device sensor 24$_1$ to be visualized or displayed on display 16 at the edge of motion box 34 graphic boundary at the point where medical device sensor 24$_1$ exited motion box 34 (displaying last valid position and orientation inside motion box). Additionally, the device status "Out of MB," or some other appropriate status identifier, will be shown on display 16. In this situation, even though medical device sensor 24$_1$ has exited motion box 34, blocks 948 and 940 typically still show the image (block 942) of medical device sensor 24$_1$ with an indicia of a valid status. For example, the user-selected color indicating valid status remains the same. Similarly, when the patient reference sensor 24$_2$ exits motion box 34, blocks 928, 930, 932 and 922, as described above, cause an image (block 926) of patient reference sensor 24$_2$ to be visualized or displayed on display 16 at the edge of motion box 34 graphic boundary at the point where patient reference sensor 24$_2$ exited motion box 34 (displaying last valid position and orientation inside motion box). Additionally, the status "Out of MB," or some other appropriate status identifier, will be shown on display 16. In this situation, even though patient reference sensor 24$_2$ has exited motion box 34, blocks 932 and 922 typically still show the image (block 926) of patient reference sensor 24$_2$ with an indicia of a valid status. For example, the green color and "top hat" shape indicating valid status remains the same.

Additionally, when a medical device sensor 24$_1$, 24$_3$ exits motion box 34, but is located at a distance less than some marginal distance or preselected nominal distance from the boundary of motion box 34 and MPS 20 still reports valid measurements of P&O of medical device sensor 24$_1$, 24$_3$ (even if potentially considered less accurate than the P&O measurements or determined while the sensor is fully within the motion box), blocks 934, 936, 938 and 940, as described above, cause an image (block 942) of medical device sensor 24$_1$, 24$_3$ at its current position and orientation (and not the last position within motion box 34) to be displayed on display 16. Similarly, when patient reference sensor 24$_2$ exits motion box 34, but is located at a distance less than some marginal distance or preselected nominal distance from the boundary of motion box 34 and MPS 20 still reports valid measurements of position and orientation (P&O) of patient reference sensor 24$_2$ (again, even if potentially considered less accurate than the P&O measurements or determined while the sensor is fully within the motion box), blocks 918, 916, 920 and 922, as described above, cause an image (block 926) of patient reference sensor 24$_2$ at its current position and orientation (and not the last position within motion box 34) to be displayed on display 16.

In the case where an invalid position and orientation of medical device sensor 24$_1$, 24$_3$ is determined by MPS 20, such that the actual position of medical device sensor 24$_1$, 24$_3$ is unknown, the device status "Out of MB," or some other appropriate status identifier, will be shown on display 16. Additionally, block 940, as described above, causes an image (block 942) of medical device sensor 24$_1$, 24$_3$ to be displayed on display 16 at the bottom of motion box 34 and the user-selected valid indicia will be altered to an indicia representing an error. For example, as shown in FIG. 7, medical device sensor 24$_1$ previously displayed in red (shown as having a spherical shape and cross-hatched in FIGS. 5A and 5B) will be displayed in amber (shown as having a spherical shape and dotted). Similarly, in the case where an invalid position and orientation of patient reference sensor 24$_2$ is determined by MPS 20, such that the actual position of patient reference sensor 24$_2$ is unknown, the status "Out of MB," or some other appropriate status identifier, will be shown on display 16.

In other embodiments, system 10 may be able to visualize or display on display 16 not only an indication that medical device sensor 24$_1$ and/or patient reference sensor 24$_2$ has exited motion box 34, but may additionally display indicia that can further aid the clinician in returning medical device sensor 24$_1$ and/or patient reference sensor 24$_2$ into motion box 34. For example, an arrow indicating the direction that medical device sensor 24$_1$ and/or patient reference sensor 24$_2$ must be moved to return into motion box 34 may be displayed on display 16.

While FIGS. 5A, 5B, 8A, and 8B illustrate only the visualization of motion box 34, patient reference sensor 24$_2$, medical device sensor 24$_1$, and thorax 50, as shown in FIGS. 10-13, in various embodiments, system 10 may be able to display additional information on display 16 alongside the visualization of motion box 34, patient reference sensor 24$_2$, medical device sensor 24$_1$, and thorax 50. For example, FIG. 10 illustrates the visualization on display 16 of a medical device being navigated into the ostium of the coronary sinus (CSOS) from the superior vena cava (SVC) alongside the visualization of the motion box 34, patient reference sensor 24$_2$, medical device sensor 24$_1$, and thorax 50. In another example, FIG. 11 illustrates the visualization on display 16 of a reconstructed 3D model of a vascular anatomical structure where contrast agent has been used alongside the visualization of the motion box 34, patient reference sensor 24$_2$, medical device sensor 24$_1$, and thorax 50. In yet another example, FIG. 12 illustrates the visualization on display 16 of fiducial-based registration using DICOM-formatted CT, MRI, or Dyna CT surface files displayed in 3D or projected on live or pre-recorded fluoroscopy images alongside the visualization of the motion box 34, patient reference sensor 24$_2$, medical device sensor 24$_1$, and thorax 50. In yet another example, FIG. 13, illustrates the visualization on display 16 of patient setup information alongside the visualization of the motion box 34, patient reference sensor 24$_2$, medical device sensor 24$_1$, and thorax 50. Furthermore, as shown in FIGS. 10-13, the ECG and respiration states, as well as whether system 10 is ready for cine capture, and message indicating whether patient reference sensor 24$_2$ or medical device sensor $24_1$ are outside of motion box 34 ("Out of MB"), may also be visualized on display 16 alongside the visualization of the motion box 34, patient reference sensor $24_2$, medical device sensor $24_1$, and thorax 50.

FIG. 14 is a schematic and block diagram of one exemplary embodiment of MPS 20, designated as an MPS 110, as also seen by reference to U.S. Pat. No. 7,386,339, referred to above, and portions of which are reproduced below, which generally describes, at least in part, the gMPS™ medical positioning system commercially offered by MediGuide Ltd. of Haifa, Israel and now owned by St. Jude Medical, Inc. It should be understood that variations are possible, for example, as also seen by reference to U.S. Pat. No. 6,233,476 entitled "Medical Positioning System," also hereby incorporated by reference in its entirety. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. Accordingly, the present description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that system 10, particularly main control 12, as described above may include conventional processing apparatus, capable of executing pre-programmed instructions stored in an associated memory, all performing in accordance with the functionality described herein. It is contemplated that the methods described herein, including without limitation the method steps of the disclosed embodiments, will be programmed in a preferred embodiment, with the resulting software being stored in an associated memory and where so described, may also constitute the means for performing such methods. Such a system may further be of the type having both ROM, RAM, a combination of non-volatile and volatile (modifiable) memory so that the software can be stored and yet allow storage and processing of dynamically produced data and/or signals.

Although numerous embodiments have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the disclosed embodiments, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

SAMPLE EMBODIMENTS

Example A

A. Medical devices, systems, and methods for displaying on a display a depiction of a position of a motion box, wherein the motion box represents a volume of physical space in which an electromagnetic sensor tracking system generates a magnetic field for measuring the position and orientation of an electromagnetic sensor tracking system-enabled sensor as described above and shown in the accompanying drawings.

Example B

B. Medical devices, systems, and methods for displaying on a display a depiction of a position of a motion box, wherein the motion box represents a volume of physical space in which an electromagnetic sensor tracking system generates a magnetic field for measuring the position and orientation of an electromagnetic sensor tracking system-enabled sensor; and for displaying on the display a depiction of the sensor electromagnetic sensor tracking system-enabled sensor in relation to the depiction of the motion box as described above and shown in the accompanying drawings.

Example C

C. A method of displaying a motion box on a display, comprising the steps of:
  measuring a position of an electromagnetic sensor tracking system, wherein the electromagnetic sensor tracking system has an electromagnetic tracking coordinate system;
  calculating an electromagnetic tracking coordinate system to a table coordinate system transformation matrix based on the measured position of the electromagnetic sensor tracking system, wherein the table coordinate system is the coordinate system of a table adapted to support a patient during a medical procedure; and
  rendering on a display a depiction of a position of the motion box, wherein the motion box represents a volume of physical space in which the electromagnetic sensor tracking system generates a magnetic field for measuring a position of a tool sensor, and wherein the rendered position of the motion box is registered to the table coordinate system.

Example D

D. The method as in example C, further comprising:
  measuring the position of the tool sensor in the electromagnetic tracking coordinate system using the electromagnetic sensor tracking system;
  transforming the position of the tool sensor from the electromagnetic tracking coordinate system to the table coordinate system using the electromagnetic coordinate system to table coordinate system transformation matrix; and
  rendering on the display a depiction of the transformed position of the tool sensor.

Example E

E. The method as in example D, further comprising rendering on the display a depiction of the transformed position of the tool sensor along a side of the motion box at a last valid measured position of the tool sensor when the tool sensor exits the motion box.

Example F

F. The method as in example D, further comprising rendering on the display a depiction of the transformed position of the tool sensor along a bottom of the motion box when the electromagnetic sensor tracking system determines an invalid position or orientation for the tool sensor.

Example G

G. The method as in example F, wherein the rendered depiction of the transformed position of the tool sensor includes an indicia indicating an invalid status.

Example H

H. The method as in example G, wherein the indicia is an amber color.

Example I

I. The method as in example C, wherein the rendered depiction of the transformed position of the motion box includes an indicia indicating one or more of a tool sensor not connected to the electromagnetic sensor tracking system and an inoperable state of the electromagnetic sensor tracking system.

Example J

J. The method as in example I, wherein the indicia is an amber color.

Example K

K. A medical navigation system, comprising:
  a display;
  a processor connected to the display;
  an electromagnetic sensor tracking system connected to the processor, the electromagnetic sensor tracking system having an electromagnetic tracking coordinate system;
  a C-Arm connected to the processor, wherein the electromagnetic sensor tracking system is affixed to the C-Arm such that the electromagnetic tracking coordinate system is in fixed relation to the C-Arm;
  a sensor, wherein the electromagnetic sensor tracking system is adapted to measure the position of the sensor in the electromagnetic tracking coordinate system; and
  a table adapted to support a patient during a medical procedure, the table having a table coordinate system;
  wherein the processor is adapted to:
    measure one or more of (1) a first rotation of the C-Arm around a caudal/cranial axis, (2) a second rotation of the C-Arm around a AP-lateral (left/right) axis, (3) a rotation of the C-Arm around a vertical (wig wag) axis, (4) a rotation of a magnetic transmitter assembly of the electromagnetic sensor tracking system around a detector axis, (5) a translation of the C-Arm, (6) a translation of the table, and (7) a source-intensifier-distance;
    calculate an electromagnetic coordinate system to a table coordinate system transformation matrix based on one or more of the measured rotations, translations and source-intensifier-distance;
    receive a measured position of the sensor in the electromagnetic tracking coordinate system from the electromagnetic sensor tracking system;
    transform the position of the sensor from the electromagnetic tracking coordinate system to the table coordinate system using the electromagnetic coordinate system to table coordinate system transformation matrix;
    render on the display a depiction of a position of a motion box, wherein the motion box represents a volume of physical space in which the electromagnetic sensor tracking system generates a magnetic field for measuring the position of the sensor, and wherein the rendered position of the motion box is registered to the table coordinate system; and
    render on the display a depiction of the transformed position of the sensor.

Example L

L. The system of example K, wherein, in the event that the sensor exits the motion box, the system is adapted to further render on the display a depiction of the transformed position of the sensor along a side of the motion box at a last valid measured position of the sensor.

What is claimed is:

1. A medical navigation system, comprising:
a processor adapted to be connected to a display;
an electromagnetic sensor tracking system connected to the processor, wherein the electromagnetic sensor tracking system has an electromagnetic tracking coordinate system, wherein the electromagnetic sensor tracking system is adapted to measure the position of a sensor located in the electromagnetic tracking coordinate system;
wherein the processor is adapted to:
measure a position of the electromagnetic sensor tracking system;
calculate an electromagnetic coordinate system to a table coordinate system transformation matrix based on the measured position of the electromagnetic sensor tracking system, wherein the table coordinate system is the coordinate system of a table adapted to support a patient during a medical procedure;
receive a measured position of the sensor in the electromagnetic tracking coordinate system from the electromagnetic sensor tracking system;
transform the position of the sensor from the electromagnetic tracking coordinate system to the table coordinate system using the electromagnetic coordinate system to table coordinate system transformation matrix; and
deliver a signal to the display to render on the display a depiction of a position of a motion box based upon the transformed position of the electromagnetic sensor tracking system, wherein the motion box depicts a volume of physical space representing boundaries of where the position of the electromagnetic sensor can be measured within a magnetic field, and wherein the rendered position of the motion box is registered to the table coordinate system.

2. The medical navigation system of claim 1, wherein the processor is further adapted to:
measure the position of the sensor in the electromagnetic tracking coordinate system using the electromagnetic sensor tracking system;
transform the position of the sensor from the electromagnetic tracking coordinate system to the table coordinate system using the electromagnetic coordinate system to table coordinate system transformation matrix; and
deliver a signal to the display to render on the display a depiction of the transformed position of the sensor.

3. The medical navigation system of claim 2, wherein the processor is further adapted to:
deliver a signal to the display to render the depiction of the transformed position of the sensor within the depiction of the motion box, when the measured position of the sensor is within the volume of physical space in which the electromagnetic sensor tracking system generates the magnetic field.

4. The medical navigation system of claim 2, wherein the sensor comprises a patient reference sensor affixed to a location on the patient and wherein the processor is further adapted to:
deliver a signal to the display to render on the display a depiction of a thorax, wherein the thorax includes a depiction of a location corresponding to the location of the patient reference sensor on the patient, and wherein the thorax is displayed in a position such that the location on the thorax corresponding to the location of the patient reference sensor on the patient is coincident with the displayed transformed position of the patient reference sensor.

5. The medical navigation system of claim 2, wherein the processor is further adapted to:
deliver a signal to the display to render on the display a depiction of the transformed position of the sensor along a side of the motion box at a last valid measured position of the sensor when the sensor exits the motion box.

6. The medical navigation system of claim 2, wherein the processor is further adapted to:
deliver a signal to the display to render on the display a depiction of the transformed position of the sensor along a bottom of the motion box when the electromagnetic sensor tracking system determines an invalid position or orientation for the sensor.

7. The medical navigation system of claim 1, wherein the electromagnetic sensor tracking system is affixed to a C-Arm such that the electromagnetic tracking coordinate system is in a fixed relation to the C-Arm; and
wherein the measured position of the electromagnetic sensor tracking system comprises a measured first rotation of the C-Arm along a caudal/cranial axis and a measured second rotation of the C-Arm along a left/right axis.

8. A method of displaying a motion box on a display, comprising the steps of:
measuring a position of an electromagnetic sensor tracking system, wherein the electromagnetic sensor tracking system has an electromagnetic tracking coordinate system;
calculating an electromagnetic tracking coordinate system to a table coordinate system transformation matrix based on the measured position of the electromagnetic sensor tracking system, wherein the table coordinate system is the coordinate system of a table adapted to support a patient during a medical procedure;
transforming the position of the electromagnetic sensor tracking system from the electromagnetic tracking coordinate system to the table coordinate system using the electromagnetic coordinate system to table coordinate system transformation matrix; and
rendering on a display a depiction of a position of the motion box based upon the transformed position of the electromagnetic sensor tracking system, wherein the motion box represents a volume of physical space depicting where the electromagnetic sensor can be measured within a magnetic field, and wherein the rendered position of the motion box is registered to the table coordinate system.

9. The method as in claim 8, wherein the rendered depiction of the transformed position of the motion box includes an indicia indicating an error state.

10. The method as in claim 9, wherein the error state comprises one or more of: a sensor not connected to the electromagnetic sensor tracking system, a position of the sensor is unknown, an orientation of the sensor is unknown, and an inoperable state of the electromagnetic sensor tracking system.

11. The method as in claim 8, further comprising the step of:
measuring the position of the sensor in the electromagnetic tracking coordinate system using the electromagnetic sensor tracking system;

transforming the position of the sensor from the electromagnetic tracking coordinate system to the table coordinate system using the electromagnetic coordinate system to table coordinate system transformation matrix; and rendering on the display a depiction of the transformed position of the sensor.

12. The method as in claim 11, wherein the depiction of the transformed position of the sensor is rendered within the depiction of the motion box, when the measured position of the sensor is within the volume of physical space in which the electromagnetic sensor tracking system generates the magnetic field.

13. The method as in claim 11, wherein the sensor comprises a patient reference sensor affixed to a location on the patient and wherein the method further comprises the step of:

rendering on the display a depiction of a thorax, wherein the thorax includes a depiction of a location corresponding to the location of the patient reference sensor on the patient, and wherein the thorax is displayed in a position such that the location on the thorax corresponding to the location of the patient reference sensor on the patient is coincident with the displayed transformed position of the patient reference sensor.

14. The method as in claim 13, wherein the thorax has a thorax coordinate system and wherein the method further comprises the step of:

transforming the orientation of the thorax from the thorax coordinate system to the table coordinate system using the transformed position of the patient reference sensor, such that the orientation of the thorax coordinate system is parallel to the table coordinate system.

15. The method as in claim 11, further comprising the step of:

rendering on the display a depiction of the transformed position of the sensor along a side of the motion box at a last valid measured position of the sensor when the sensor exits the motion box.

16. The method as in claim 11, further comprising the step of:

rendering on the display a depiction of the transformed position of the sensor along a bottom of the motion box when the electromagnetic sensor tracking system determines an invalid position or orientation for the sensor.

17. The method as in claim 16, wherein the rendered depiction of the transformed position of the sensor includes an indicia indicating an invalid status.

18. The method as in claim 11, wherein the sensor comprises one or more of a patient reference sensor affixed to a patient and a medical device sensor on a medical device.

19. The method as in claim 11, further comprising the step of:

measuring the orientation of the sensor in the electromagnetic tracking coordinate system using the electromagnetic sensor tracking system; and rendering on the display a depiction of the orientation of the sensor.

20. The method as in claim 8, wherein the electromagnetic sensor tracking system is affixed to a C-Arm such that the electromagnetic tracking coordinate system is in a fixed relation to the C-Arm; and wherein the step of measuring the position of the electromagnetic sensor tracking system comprises measuring a first rotation of the C-Arm along a caudal/cranial axis and measuring a second rotation of the C-Arm along a left/right axis.

* * * * *